US012582614B2

(12) United States Patent
Kwon et al.

(10) Patent No.: US 12,582,614 B2
(45) Date of Patent: Mar. 24, 2026

(54) COMPOSITION FOR PREVENTING, ALLEVIATING OR TREATING SARCOPENIA, CONTAINING D-RIBO-2-HEXULOSE AS ACTIVE INGREDIENT

(71) Applicant: KYUNGPOOK NATIONAL UNIVERSITY INDUSTRY-ACADEMIC COOPERATION FOUNDATION, Daegu (KR)

(72) Inventors: Eun-Young Kwon, Daegu (KR); Youngji Han, Daegu (KR); Ji-Eun Kim, Daegu (KR)

(73) Assignee: KYUNGPOOK NATIONAL UNIVERSITY INDUSTRY-ACADEMIC COOPERATION FOUNDATION, Daegu (KR)

( * ) Notice: Subject to any disclaimer, the term of this patent is extended or adjusted under 35 U.S.C. 154(b) by 394 days.

(21) Appl. No.: 18/548,717

(22) PCT Filed: Mar. 4, 2022

(86) PCT No.: PCT/KR2022/003104
§ 371 (c)(1),
(2) Date: Sep. 1, 2023

(87) PCT Pub. No.: WO2022/186658
PCT Pub. Date: Sep. 9, 2022

(65) Prior Publication Data
US 2024/0139122 A1 May 2, 2024

(30) Foreign Application Priority Data

Mar. 4, 2021 (KR) ........................ 10-2021-0029041
Mar. 4, 2022 (KR) ........................ 10-2022-0027780

(51) Int. Cl.
*A61K 31/047* (2006.01)
*A61P 21/00* (2006.01)

(52) U.S. Cl.
CPC ............ *A61K 31/047* (2013.01); *A61P 21/00* (2018.01)

(58) Field of Classification Search
CPC .................................................. A61K 31/047
See application file for complete search history.

(56) References Cited

U.S. PATENT DOCUMENTS

| 6,051,236 A | 4/2000 | Portman |
| 8,071,558 B2 | 12/2011 | Tokuda |
| 2012/0329735 A1 | 12/2012 | Sato |

FOREIGN PATENT DOCUMENTS

| CN | 108653298 | 10/2018 |
| EP | 3701953 A1 | 9/2020 |
| JP | 2005263734 | 9/2005 |

OTHER PUBLICATIONS

Han, Y., et al., "Tracing the Anti-Inflammatory Mechanism/Triggers of d-Allulose: A Profile Study of Microbiome Composition and mRNA Expression in Diet-Induced Obese Mice", Molecular Nutrition & Food Research, col. 64, No. 5 (Dec. 17, 2019), Aricle 1900982.

Kim J.-E., et al., "Allulose Attenuated Age-Associated Sarcopenia via Regulating IGF-1 and Myostatin in Aged Mice", Molecular Nutrition & Food Research, vol. 66, No. 1 (Nov. 17, 2021), Article e2100549.

Matsuo, T., et al., "The effects of 90-day feeding of D-psicose syrup in male Wistar rats," Open Journal of Preventive Medicine , vol. 1, No. 2 (2011), pp. 66-71.

Ochiai, M., et al., "D-Psicose increases energy expenditure and decreases body fat accumulation in rats fed a high-sucrose diet," vol. 65, No. 2 (2014), pp. 245-250.

Pongkan , W., et al., "d-allulose provides cardioprotective effect by attenuating cardiac mitochondrial dysfunction in obesity-induced insulin-resistant rats", European Journal of Nutrition, vol. 60, No. 4 (Oct. 3, 2020), pp. 2047-2061.

Coll, Patrick P., et al. "The prevention of osteoporosis and sarcopenia in older adults." Journal of the American Geriatrics Society 69.5 (2021): 1388-1398.

Itoh, Kouichi, et al. "Beneficial effects of supplementation of the rare sugar "D-allulose" against hepatic steatosis and severe obesity in lepob/lepob mice." Journal of food science 80.7 (2015): H1619-H1626.

*Primary Examiner* — Yong S. Chong
(74) *Attorney, Agent, or Firm* — Riverside Law LLP

(57) ABSTRACT

The present invention relates to a composition for preventing, alleviating or treating sarcopenia, containing D-ribo-2-hexulose as an active ingredient. D-ribo-2-hexulose of the present invention is a sweetener capable of replacing sugar, is harmless to the human body and does not cause side effects in normal cells so as to be safe for the human body, inhibits the degradation of myoproteins, and can exhibit muscle strengthening effects by increasing muscle mass, and thus the present invention is expected to be effectively usable in the prevention, alleviation or treatment of sarcopenia.

4 Claims, 18 Drawing Sheets
Specification includes a Sequence Listing.

SEQUENCE LISTING

```
<160> NUMBER OF SEQ ID NOS: 34

<210> SEQ ID NO 1
<211> LENGTH: 20
<212> TYPE: DNA
<213> ORGANISM: Artificial Sequence
<220> FEATURE:
<223> OTHER INFORMATION: GAPDH_F

<400> SEQUENCE: 1
tgcagtggca aagtggagat                                              20

<210> SEQ ID NO 2
<211> LENGTH: 20
<212> TYPE: DNA
<213> ORGANISM: Artificial Sequence
<220> FEATURE:
<223> OTHER INFORMATION: GAPDH_R

<400> SEQUENCE: 2
ttgaatttgc cgtgagtgga                                              20

<210> SEQ ID NO 3
<211> LENGTH: 24
<212> TYPE: DNA
<213> ORGANISM: Artificial Sequence
<220> FEATURE:
<223> OTHER INFORMATION: Atrogin-1_F

<400> SEQUENCE: 3
aaccgggagg ccagctaaag aaca                                         24

<210> SEQ ID NO 4
<211> LENGTH: 23
<212> TYPE: DNA
<213> ORGANISM: Artificial Sequence
<220> FEATURE:
<223> OTHER INFORMATION: Atrogin-1_R
```

-continued

<400> SEQUENCE: 4
tgggcctaca gaacagacag tgc                                          23

<210> SEQ ID NO 5
<211> LENGTH: 19
<212> TYPE: DNA
<213> ORGANISM: Artificial Sequence
<220> FEATURE:
<223> OTHER INFORMATION: FoxO3_F

<400> SEQUENCE: 5
tcgcctcctg gcgggctta                                              19

<210> SEQ ID NO 6
<211> LENGTH: 20
<212> TYPE: DNA
<213> ORGANISM: Artificial Sequence
<220> FEATURE:
<223> OTHER INFORMATION: FoxO3_R

<400> SEQUENCE: 6
acggcggtgc tagcctgaga                                             20

<210> SEQ ID NO 7
<211> LENGTH: 28
<212> TYPE: DNA
<213> ORGANISM: Artificial Sequence
<220> FEATURE:
<223> OTHER INFORMATION: Mef2_F

<400> SEQUENCE: 7
acacgcataa tggatgagag gaaccgac                                    28

<210> SEQ ID NO 8
<211> LENGTH: 28
<212> TYPE: DNA
<213> ORGANISM: Artificial Sequence
<220> FEATURE:
<223> OTHER INFORMATION: Mef2_R

<400> SEQUENCE: 8
caacgatatc cgagttcgtc ctgctttc                                    28

<210> SEQ ID NO 9
<211> LENGTH: 20
<212> TYPE: DNA
<213> ORGANISM: Artificial Sequence
<220> FEATURE:
<223> OTHER INFORMATION: Myf5_F

<400> SEQUENCE: 9
aggaaaagaa gccctgaagc                                             20

<210> SEQ ID NO 10
<211> LENGTH: 20
<212> TYPE: DNA
<213> ORGANISM: Artificial Sequence
<220> FEATURE:
<223> OTHER INFORMATION: Myf5_R

<400> SEQUENCE: 10
gcaaaaagaa caggcagagg                                             20

<210> SEQ ID NO 11

-continued

```
<211> LENGTH: 22
<212> TYPE: DNA
<213> ORGANISM: Artificial Sequence
<220> FEATURE:
<223> OTHER INFORMATION: Myf6_F

<400> SEQUENCE: 11
caagaaaatc ttgagggtgc gg                                          22

<210> SEQ ID NO 12
<211> LENGTH: 20
<212> TYPE: DNA
<213> ORGANISM: Artificial Sequence
<220> FEATURE:
<223> OTHER INFORMATION: Myf6_R

<400> SEQUENCE: 12
ttagccgtta tcacgagccc                                             20

<210> SEQ ID NO 13
<211> LENGTH: 20
<212> TYPE: DNA
<213> ORGANISM: Artificial Sequence
<220> FEATURE:
<223> OTHER INFORMATION: MyoD_F

<400> SEQUENCE: 13
gcttctatcg ccgccactcc                                             20

<210> SEQ ID NO 14
<211> LENGTH: 20
<212> TYPE: DNA
<213> ORGANISM: Artificial Sequence
<220> FEATURE:
<223> OTHER INFORMATION: MyoD_R

<400> SEQUENCE: 14
cgcacatgct catcctcacg                                             20

<210> SEQ ID NO 15
<211> LENGTH: 18
<212> TYPE: DNA
<213> ORGANISM: Artificial Sequence
<220> FEATURE:
<223> OTHER INFORMATION: Myogenin_F

<400> SEQUENCE: 15
ccttgctcag ctccctca                                               18

<210> SEQ ID NO 16
<211> LENGTH: 19
<212> TYPE: DNA
<213> ORGANISM: Artificial Sequence
<220> FEATURE:
<223> OTHER INFORMATION: Myogenin_R

<400> SEQUENCE: 16
tgggagttgc attcactgg                                              19

<210> SEQ ID NO 17
<211> LENGTH: 20
<212> TYPE: DNA
<213> ORGANISM: Artificial Sequence
<220> FEATURE:
<223> OTHER INFORMATION: MuRF1_F

<400> SEQUENCE: 17
```

```
gagaacctgg agaagcagct                                              20

<210> SEQ ID NO 18
<211> LENGTH: 18
<212> TYPE: DNA
<213> ORGANISM: Artificial Sequence
<220> FEATURE:
<223> OTHER INFORMATION: MuRF1_R

<400> SEQUENCE: 18
ccgcggttgg tccagtag                                                18

<210> SEQ ID NO 19
<211> LENGTH: 17
<212> TYPE: DNA
<213> ORGANISM: Artificial Sequence
<220> FEATURE:
<223> OTHER INFORMATION: CerS1_F

<400> SEQUENCE: 19
gcagccacca cacacat                                                 17

<210> SEQ ID NO 20
<211> LENGTH: 20
<212> TYPE: DNA
<213> ORGANISM: Artificial Sequence
<220> FEATURE:
<223> OTHER INFORMATION: CerS1_R

<400> SEQUENCE: 20
atgcctgacc tccagtcata                                              20

<210> SEQ ID NO 21
<211> LENGTH: 20
<212> TYPE: DNA
<213> ORGANISM: Artificial Sequence
<220> FEATURE:
<223> OTHER INFORMATION: CIDEC_F

<400> SEQUENCE: 21
tccaggacat cttgaaactt                                              20

<210> SEQ ID NO 22
<211> LENGTH: 21
<212> TYPE: DNA
<213> ORGANISM: Artificial Sequence
<220> FEATURE:
<223> OTHER INFORMATION: CIDEC_R

<400> SEQUENCE: 22
ggcttgcaag tattcttctg t                                            21

<210> SEQ ID NO 23
<211> LENGTH: 22
<212> TYPE: DNA
<213> ORGANISM: Artificial Sequence
<220> FEATURE:
<223> OTHER INFORMATION: CISH_F

<400> SEQUENCE: 23
ggacatggtc ctttgcgtac ag                                           22

<210> SEQ ID NO 24
<211> LENGTH: 22
<212> TYPE: DNA
```

-continued

<213> ORGANISM: Artificial Sequence
<220> FEATURE:
<223> OTHER INFORMATION: CISH_R

<400> SEQUENCE: 24
ggagaacgtc ttggctatgc ac                                       22

<210> SEQ ID NO 25
<211> LENGTH: 20
<212> TYPE: DNA
<213> ORGANISM: Artificial Sequence
<220> FEATURE:
<223> OTHER INFORMATION: SCD1_F

<400> SEQUENCE: 25
tcctgctcat gtgcttcatc                                          20

<210> SEQ ID NO 26
<211> LENGTH: 20
<212> TYPE: DNA
<213> ORGANISM: Artificial Sequence
<220> FEATURE:
<223> OTHER INFORMATION: SCD1_R

<400> SEQUENCE: 26
ggatgttctc ccgagattga                                          20

<210> SEQ ID NO 27
<211> LENGTH: 19
<212> TYPE: DNA
<213> ORGANISM: Artificial Sequence
<220> FEATURE:
<223> OTHER INFORMATION: Adipsin_F

<400> SEQUENCE: 27
aaccggacaa cctgcaatc                                           19

<210> SEQ ID NO 28
<211> LENGTH: 19
<212> TYPE: DNA
<213> ORGANISM: Artificial Sequence
<220> FEATURE:
<223> OTHER INFORMATION: Adipsin_R

<400> SEQUENCE: 28
cccacgtaac cacaccttc                                           19

<210> SEQ ID NO 29
<211> LENGTH: 18
<212> TYPE: DNA
<213> ORGANISM: Artificial Sequence
<220> FEATURE:
<223> OTHER INFORMATION: Adiponectin_F

<400> SEQUENCE: 29
ccgttcagca ttcagtgt                                            18

<210> SEQ ID NO 30
<211> LENGTH: 19
<212> TYPE: DNA
<213> ORGANISM: Artificial Sequence
<220> FEATURE:
<223> OTHER INFORMATION: Adiponectin_R

<400> SEQUENCE: 30
cagccttgtc cttcttgta                                           19

-continued

```
<210> SEQ ID NO 31
<211> LENGTH: 21
<212> TYPE: DNA
<213> ORGANISM: Artificial Sequence
<220> FEATURE:
<223> OTHER INFORMATION: Haptoglobin_F

<400> SEQUENCE: 31
ctgtggagtt gggcaatgat g                                           21

<210> SEQ ID NO 32
<211> LENGTH: 21
<212> TYPE: DNA
<213> ORGANISM: Artificial Sequence
<220> FEATURE:
<223> OTHER INFORMATION: Haptoglobin_R

<400> SEQUENCE: 32
aaccaagtgc tccacatagc c                                           21

<210> SEQ ID NO 33
<211> LENGTH: 20
<212> TYPE: DNA
<213> ORGANISM: Artificial Sequence
<220> FEATURE:
<223> OTHER INFORMATION: Neuronatin_F

<400> SEQUENCE: 33
gctcatcatc ggctggtaca                                             20

<210> SEQ ID NO 34
<211> LENGTH: 20
<212> TYPE: DNA
<213> ORGANISM: Artificial Sequence
<220> FEATURE:
<223> OTHER INFORMATION: Neuronatin_R

<400> SEQUENCE: 34
cttggcaagt gctcctctga                                             20
```

COMPOSITION FOR PREVENTING, ALLEVIATING OR TREATING SARCOPENIA, CONTAINING D-RIBO-2-HEXULOSE AS ACTIVE INGREDIENT

CROSS-REFERENCE TO RELATED APPLICATIONS

This application is a U.S. national phase application filed under 35 U.S.C. § 371 claiming benefit to International Patent Application No. PCT/KR2022/003104, filed on Mar. 4, 2022, which claims priority to Korean Application No. 10-2021-0029041, filed on Mar. 4, 2021, and Korean Application No. 10-2022-0027780, filed on Mar. 4, 2022, the disclosures of each of which are incorporated by reference herein in their entirety.

REFERENCE TO A "SEQUENCE LISTING," A TABLE, OR A COMPUTER PROGRAM LISTING APPENDIX SUBMITTED AS AN ASCII TEXT FILE

The present application hereby incorporates by reference the entire contents of the text file named "206132-0148-00US_SequenceListing.txt" in ASCII format, which was created on Sep. 1, 2023, and is 7,036 bytes in size.

TECHNICAL FIELD

The present invention relates to a composition for treating, alleviating or treating sarcopenia, including D-ribo-2-hexulose as an active ingredient.

BACKGROUND ART

Sarcopenia is a disease in which muscle mass abnormally and rapidly decreases, unlike the loss of muscle that occurs in the normal aging process, and is known to appear as the number and differentiation potential of adult muscle stem cells known as satellite cells gradually decrease with age.

The World Health Organization (WHO) newly assigned a disease classification code to sarcopenia in October 2016 and officially classified it as a new geriatric disease. The prevalence of sarcopenia is 13 to 24% in people under the age of 70, but the incidence increases to more than 50% in those over 80 years of age. When a person has sarcopenia, decreases in muscle mass, exercise power, and muscle strength may be caused, thereby making it difficult to live independently and difficult to improve from other diseases such as brain diseases, heart diseases, diabetes, and the like. Therefore, it has been gradually recognized that sarcopenia has an important effect on the quality of life in old age.

Meanwhile, D-ribo-2-hexulose is a C-3 epimer of D-fructose that is a natural sugar that is present in a very small amount in a commercial mixture of D-glucose and D-fructose obtained from the hydrolysis of sucrose or the isomerization of D-glucose, and is a monosaccharide with a degree of sweetness of 70% compared to sugar. D-ribo-2-hexulose has almost no calories because it is not metabolized in the human body, and has been reported as a sweetener that has a relatively small effect on weight gain due to its action of inhibiting the formation of body fat. In recent years, since the effect of D-ribo-2-hexulose on the non-cariogenic and anti-cariogenic functions has been announced, a substance that helps dental health is being actively developed as a sweetener capable of replacing sugar. As described above, D-ribo-2-hexulose has come into the spotlight in the food industry as a sweetener for preventing weight gain due to its characteristics and functionalities. However, D-ribo-2-hexulose is not easy to chemically synthesize because a very small amount of D-ribo-2-hexulose is converted from fructose at a high temperature. Therefore, research has been conducted on a method capable of mass-producing D-ribo-2-hexulose. As one example, a method of reacting fructose with a D-tagatose epimerase, a method of reacting fructose with a D-ribo-2-hexulose epimerase, or a method of mass-producing D-ribo-2-hexulose from the hydrolysis of sucrose or isomerization of D-glucose using an enzymatic method has been reported.

D-ribo-2-hexulose is a substance considered as generally recognized as safe (GRAS) by the United States Department of Agriculture (USDA). In this regard, studies have reported that D-ribo-2-hexulose has an effect on lipid metabolism, but the specific effects of D-ribo-2-hexulose in relation to sarcopenia, which is a new senile disease, have not been identified.

DISCLOSURE

Technical Problem

The present inventors have made intensive efforts to develop an agent that can effectively treat sarcopenia or effectively slow the progression of sarcopenia, and found that D-ribo-2-hexulose, which is a type of monosaccharide, may efficiently alleviate sarcopenia by increasing muscle mass and strength without exercise in aged mice having difficulty in exercising. Therefore, the present invention has been completed based on these facts.

Therefore, it is an object of the present invention to provide a pharmaceutical composition for preventing or treating sarcopenia, comprising D-ribo-2-hexulose as an active ingredient.

It is another object of the present invention to provide a food composition for preventing or alleviating sarcopenia, comprising D-ribo-2-hexulose as an active ingredient.

However, the technical objects to be achieved by the present invention are not limited to the aforementioned technical objects, and other objects which are not mentioned above will be clearly understood from the following detailed description by those skilled in the art to which the present invention belongs.

Technical Solution

To achieve the above objects, according to an aspect of the present invention, there is provided a pharmaceutical composition for preventing or treating sarcopenia, comprising D-ribo-2-hexulose as an active ingredient.

According to another aspect of the present invention, there is provided a food composition for preventing or alleviating sarcopenia, comprising D-ribo-2-hexulose as an active ingredient.

According to one exemplary embodiment of the present invention, the D-ribo-2-hexulose may satisfy one or more of the following characteristics, but the present invention is not limited thereto:

a) increasing the expression of insulin-like growth factor 1 (IGF-1);

b) inhibiting myostatin expression;

c) inhibiting a reduction in muscle strength; or d) increasing muscle mass.

According to another exemplary embodiment of the present invention, the food composition may be a health functional food composition, but the present invention is not limited thereto.

According to still another aspect of the present invention, there is provided a method of preventing or treating sarcopenia, which includes: administering the composition comprising D-ribo-2-hexulose as an active ingredient to a subject in need thereof.

According to yet another aspect of the present invention, there is provided a use of the composition comprising D-ribo-2-hexulose as an active ingredient for the prevention or treatment of sarcopenia.

According to yet another aspect of the present invention, there is provided a use of D-ribo-2-hexulose for the manufacture of a drug for the treatment of sarcopenia.

Advantageous Effects

D-ribo-2-hexose of the present invention is a sweetener capable of replacing sugar, is harmless to the human body, does not cause side effects in normal cells, thereby being safe for e human body, and can inhibit the degradation of myoprotein, and exhibit a muscle strength strengthening effect through an increase in muscle mass. Therefore, the present invention is expected to be effectively used in the prevention, alleviation or treatment of sarcopenia.

(CerS1) in the mice of the NC and DRH groups through mRNA sequencing and RT-PCR.

Figures 3, 3A:
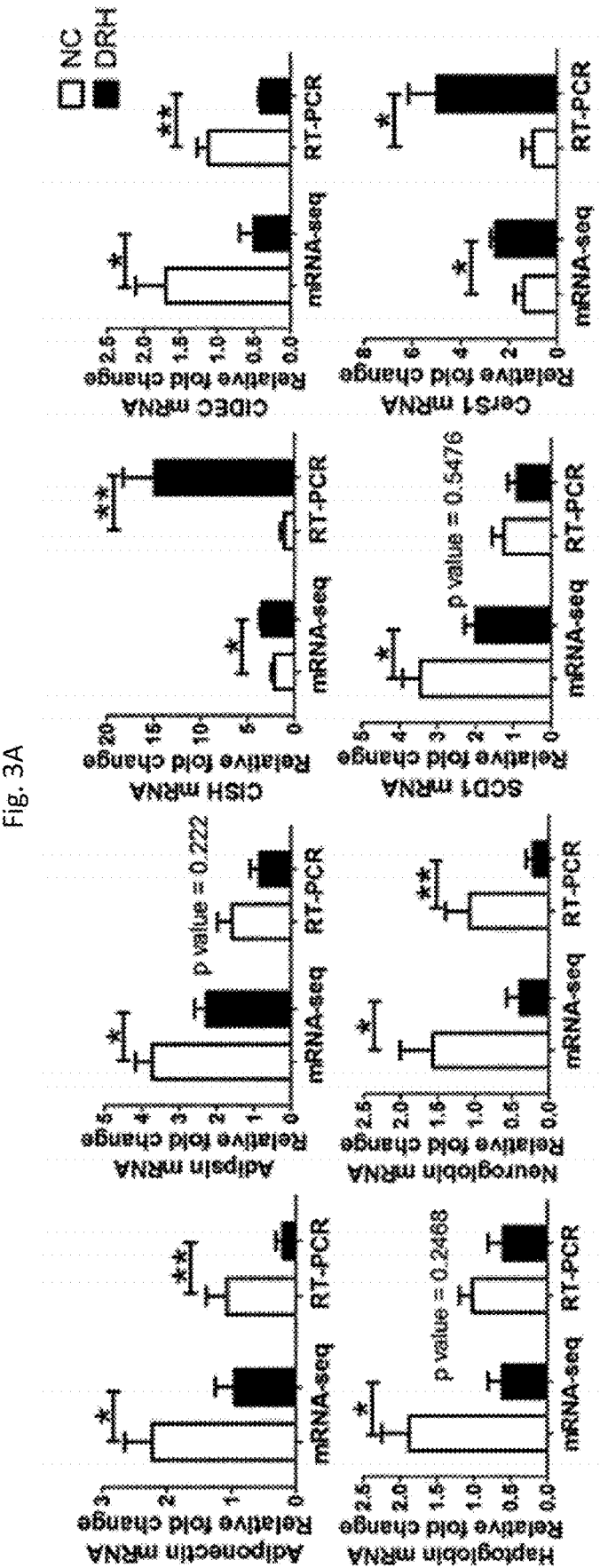
FIG. 3A is a diagram showing the results of confirming the expression of adiponectin, adipsin, a cytokine inducible SH2-containing protein (CISH), cell death-inducing DFFA-like effector c (CIDEC), haptoglobin, neuronatin, stearoyl-coenzyme A desaturase 1 (SCD1), and ceramide synthase 1
Figures 3, 3B:
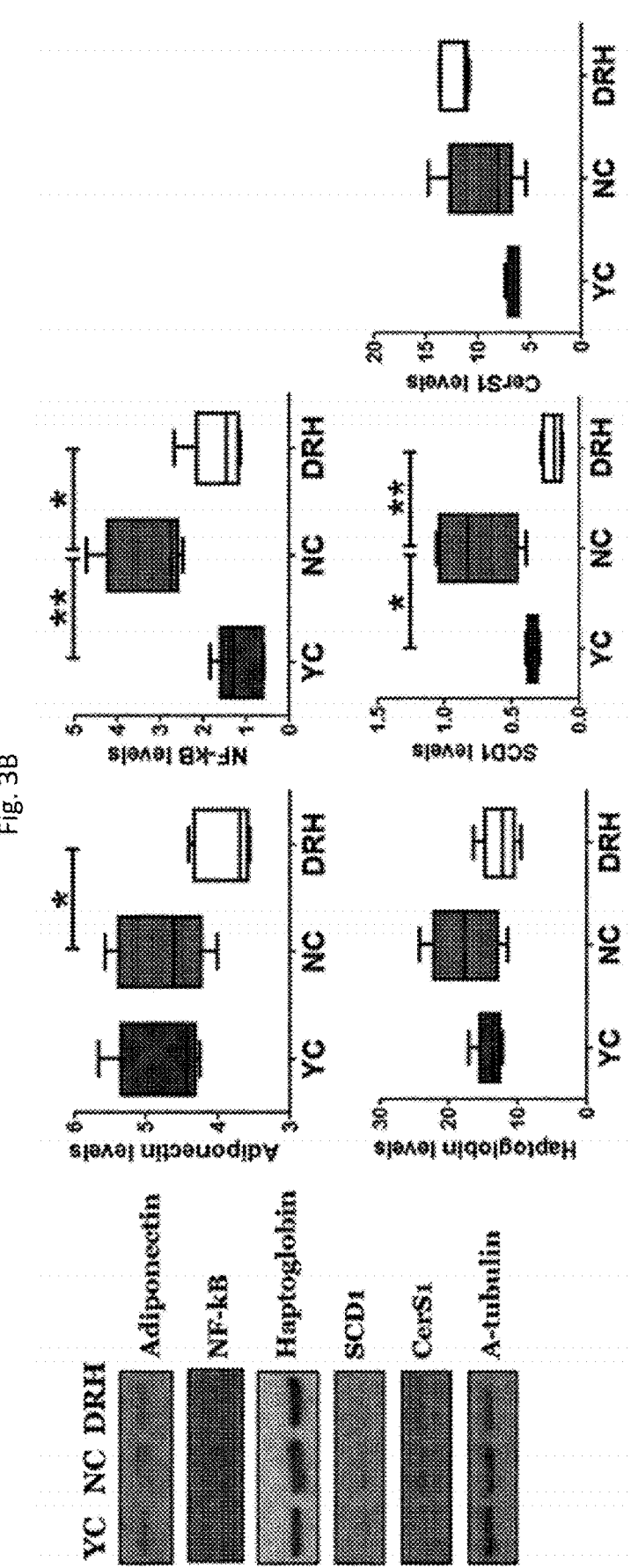

FIG. 3B is a diagram showing the results of confirming the expression of adiponectin, NF-kappa B (NF-κB), haptoglobin, and ceramide synthase 1 (CerS1), which are differentially expressed in the mice of the DRH group compared to the mice of the NC group, through Western blotting.

Figures 3, 3C:
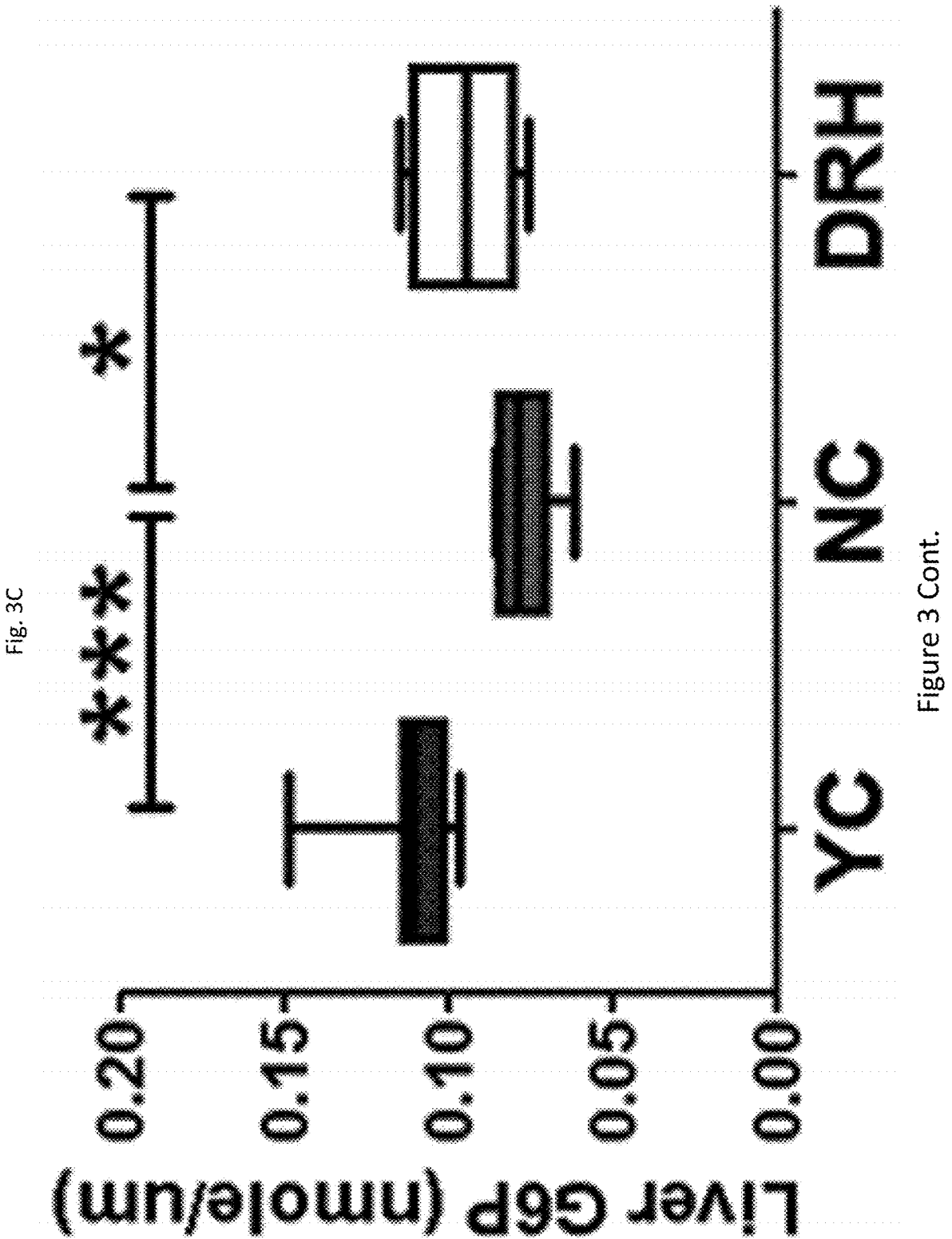

FIG. 3C is a diagram showing the results of measuring hepatic glucose-6-phosphatase (G6P) in the mice of the YC, NC, and DRH groups.

Figures 3, 3D:
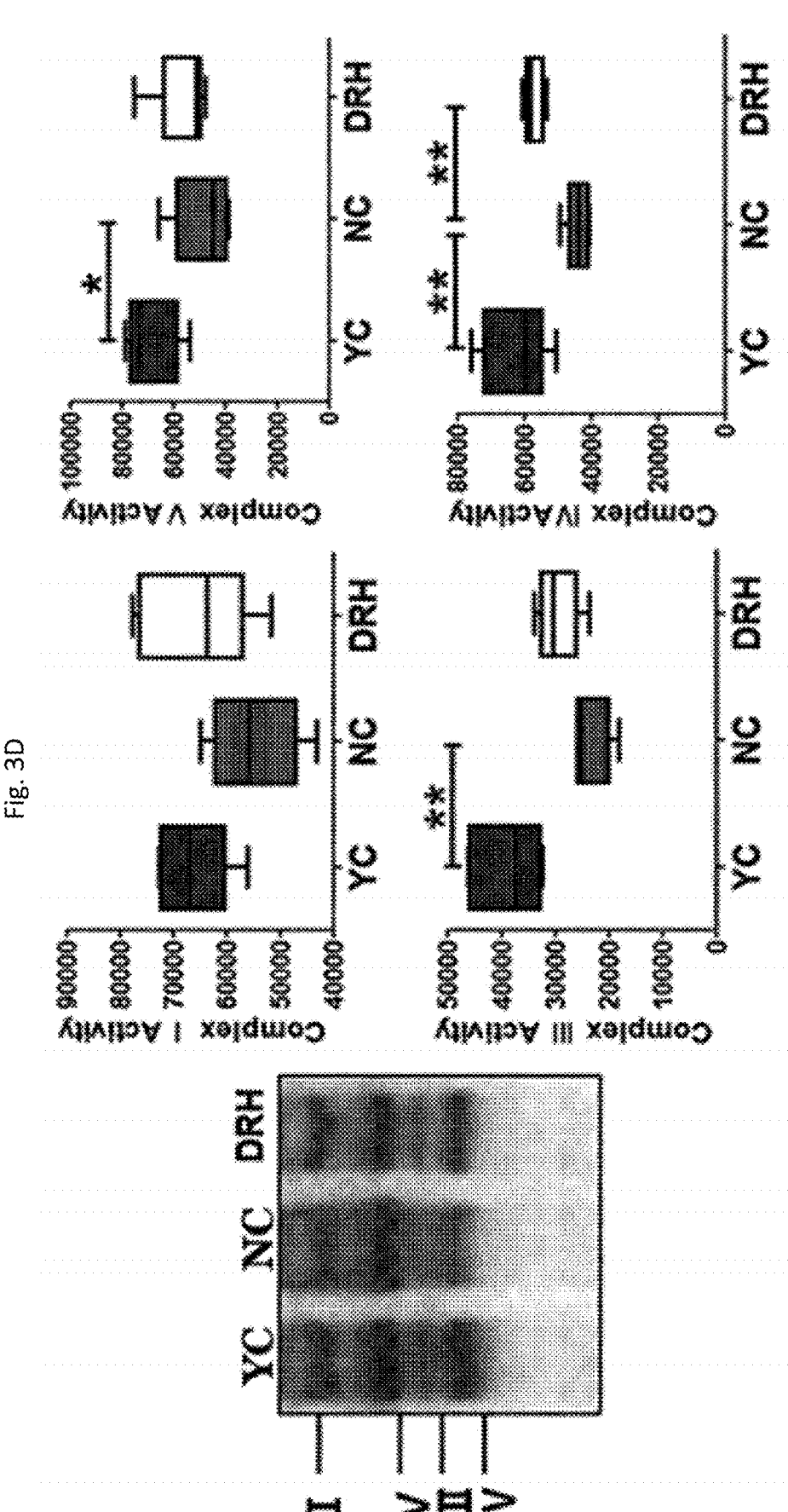

FIG. 3D is a diagram showing the results of confirming the activity of a mitochondrial respiratory chain complex in the mice of the YC, NC, and DRH groups through BN-PAGE.

Figures 4, 4A:
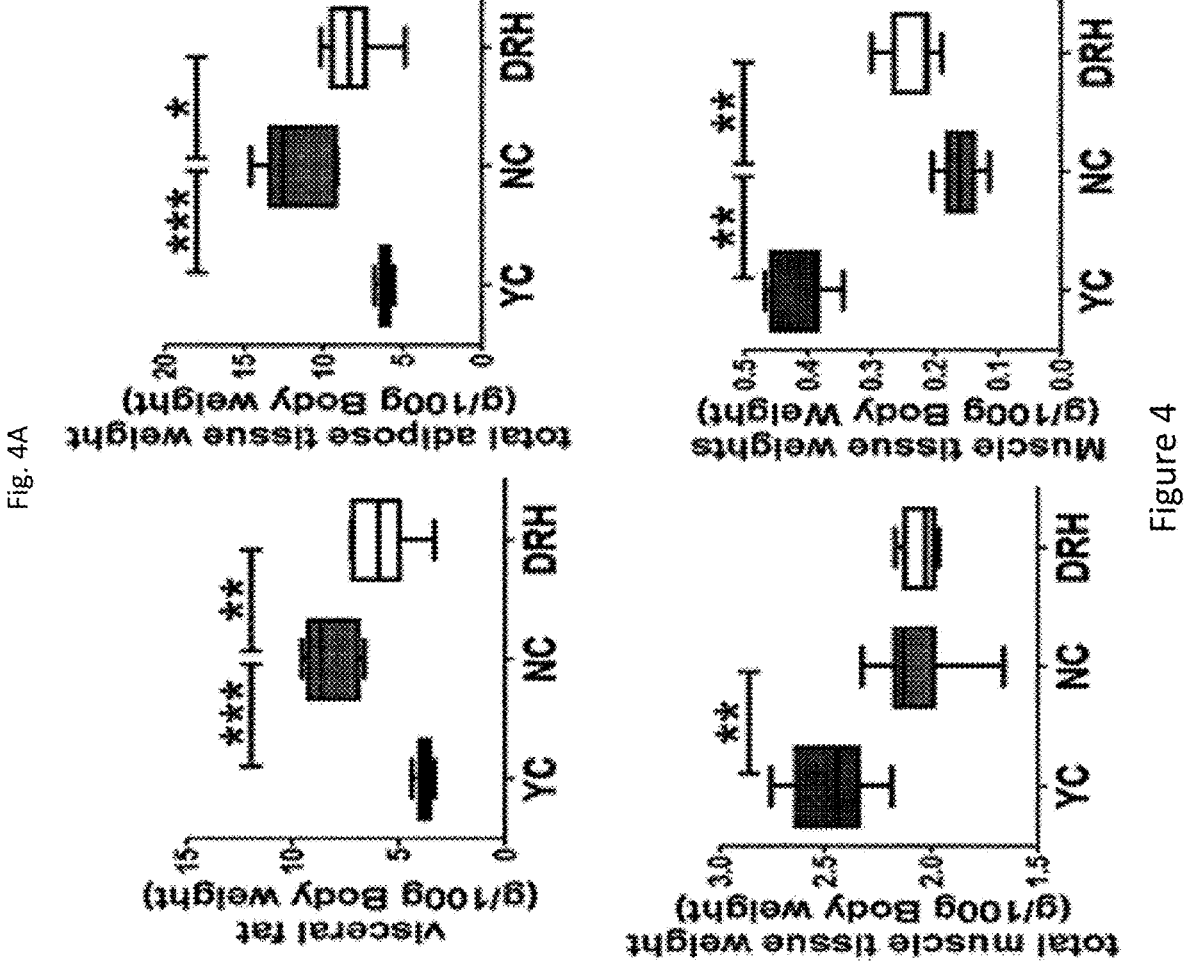

FIG. 4A is a diagram showing the results of confirming the visceral fat, the total adipose tissue weight, the total muscle tissue weight, and the muscle tissue weight per 100 g of body weight in the mice of the YC, NC, and DRH groups.

Figures 4, 4B:
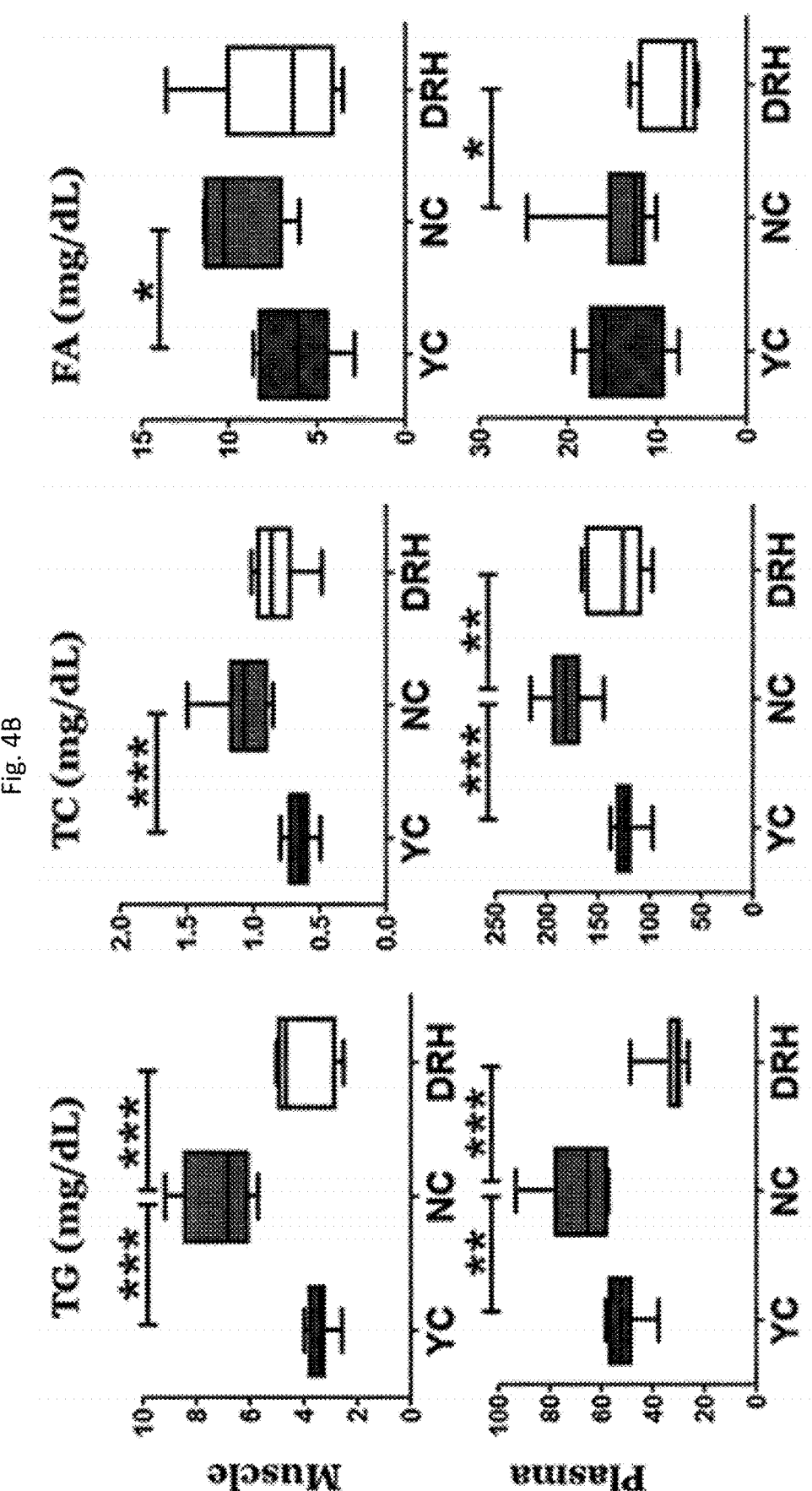

FIG. 4B is a diagram confirming the lipid profiles of muscles and plasma in the mice of the YC, NC, and DRH groups (TG: triglyceride, TC: total cholesterol, and FA: fatty acid).

Figures 5, 5A:
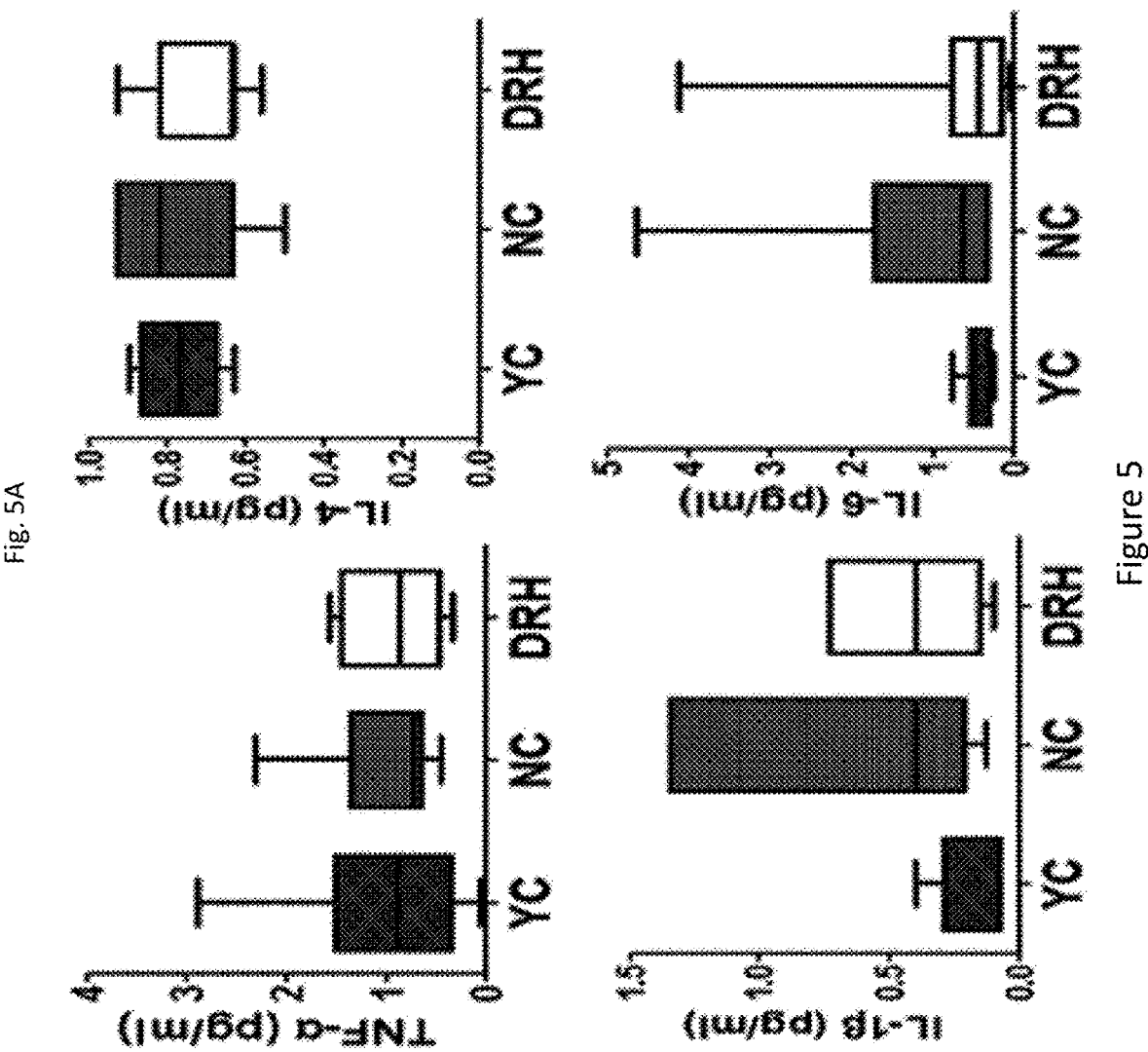

FIG. 5A is a diagram showing the results of measuring the levels of inflammatory cytokines TNF-α, IL-4, IL-1β, and IL-6 in the mice of the YC, NC, and DRH groups.

Figures 5, 5B:
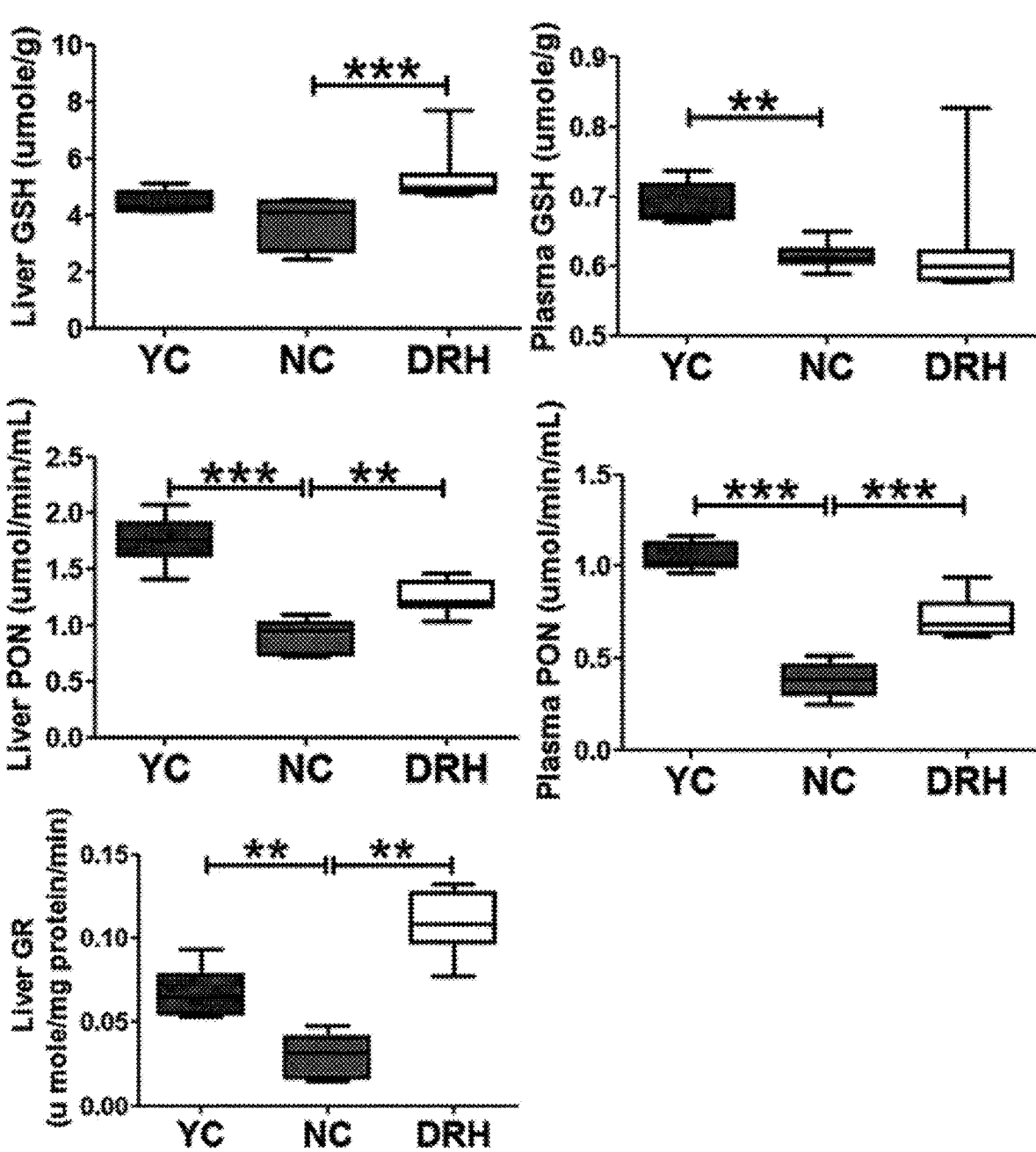

FIG. 5B is a diagram showing the results of confirming liver GSH, PON and GR activity, and plasma GSH and PON activity in the mice of the YC, NC, and DRH groups.

Figures 5, 5C:
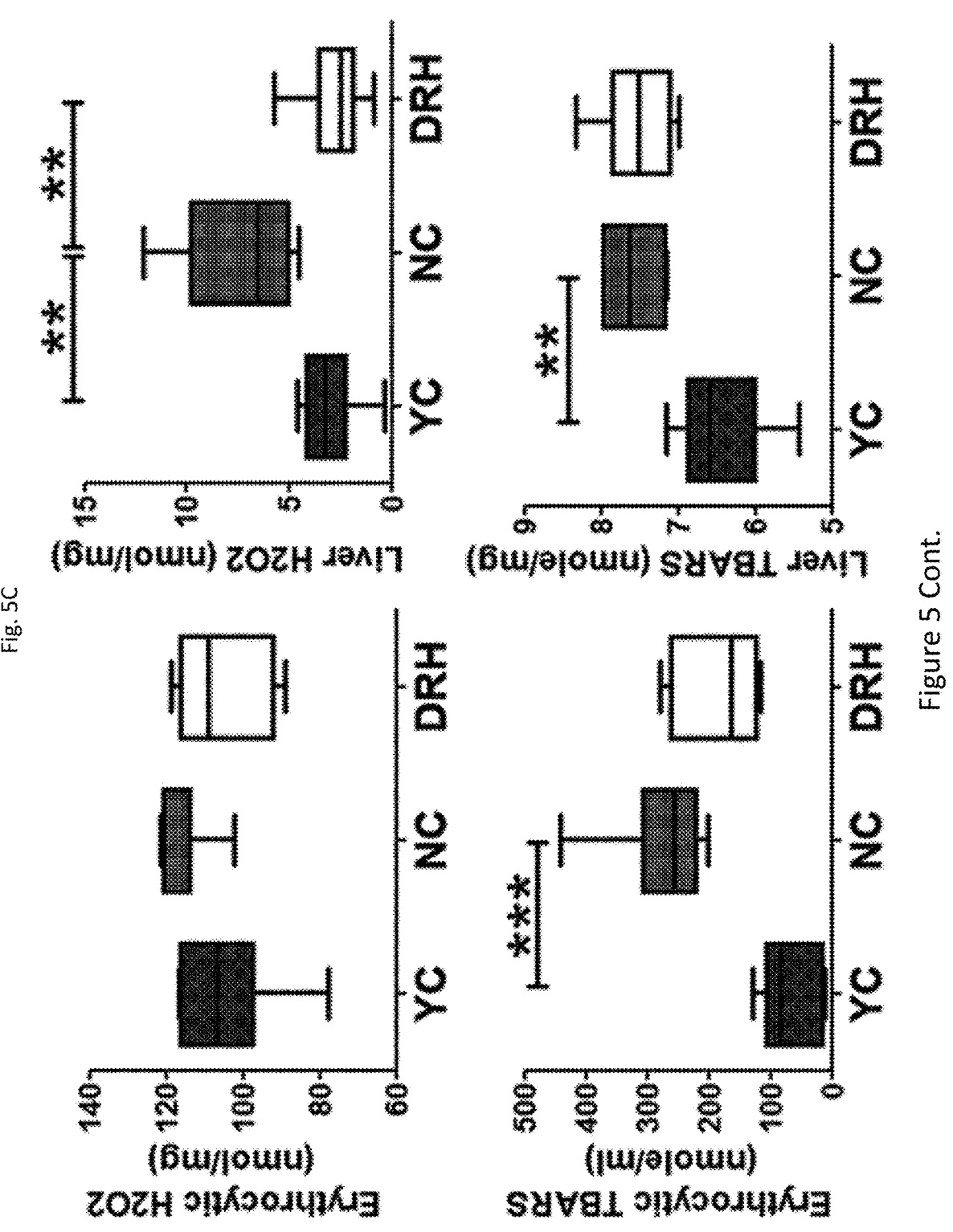

FIG. 5C is a diagram showing the results of measuring liver and erythrocytic $H_2O_2$ contents and thiobarbituric acid reactive substance (TBARs) activity in the mice of the YC, NC, and DRH groups.

Figures 5, 5D:
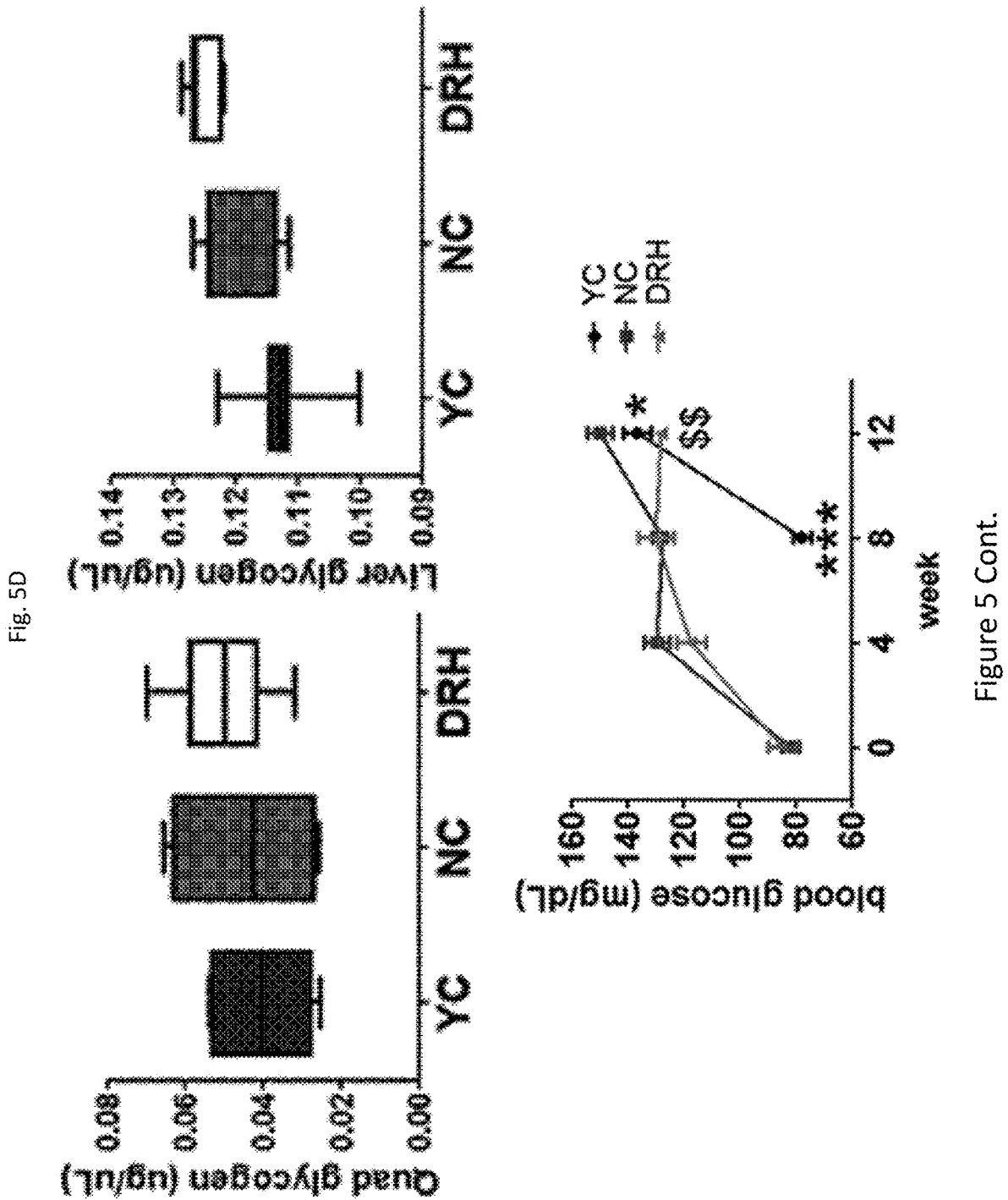

FIG. 5D is a diagram showing the results of measuring muscle (quadriceps; quad) and liver glycogen contents, and fasting blood glucose in the mice of the YC, NC, and DRH groups.

Figures 5, 5E:
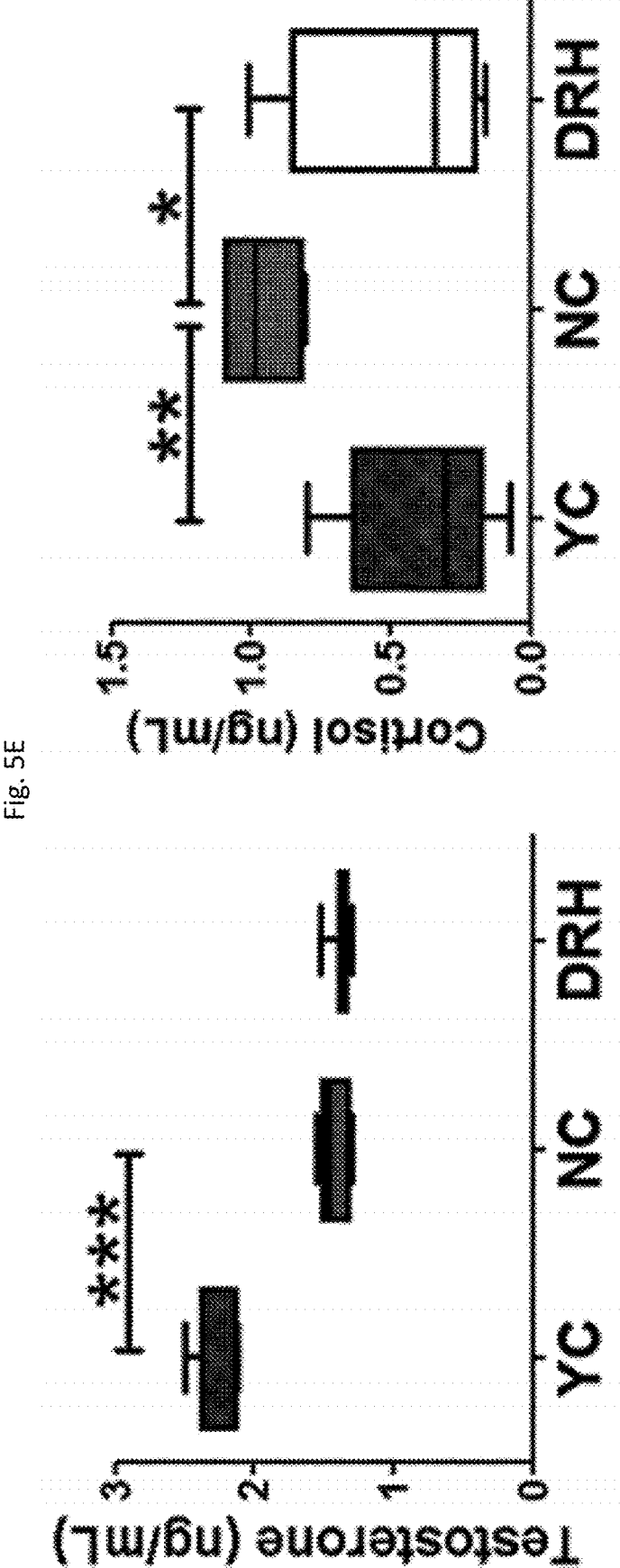

FIG. 5E is a diagram showing the results of measuring the levels of testosterone and cortisol in the mice of the YC, NC, and DRH groups.

BEST MODE

The present inventors have made intensive efforts to develop an agent that can effectively treat sarcopenia or effectively slow the progression of sarcopenia, and found that D-ribo-2-hexulose, which is a type of monosaccharide, increases muscle mass and strength without exercise in aged mice having difficulty in exercising. Therefore, the present invention has been completed based on these facts.

Hereinafter, the present invention will be described in detail.

The present invention provides a pharmaceutical composition for preventing or treating sarcopenia, which comprises D-ribo-2-hexulose as an active ingredient.

In this specification, the term "sarcopenia" refers to a disease in which skeletal muscle mass gradually decreases and muscle density and function are gradually weakened with aging, and directly causes a decrease in muscle strength, which results in various physical dysfunctions and disabilities.

In the present invention, the composition may be used for people in their 30s or older, people in their 40s or older, people in their 50s or older, people in their 60s or older, people in their 70s or older, or people in their 80s or older, who are suspected of having sarcopenia, but the present invention is not limited thereto. Also, the composition may be used for people over the age of 26 who have a gradual decrease in skeletal muscle mass or a gradual decline in muscle density and function.

According to one embodiment of the present invention, it was confirmed that D-ribo-2-hexulose may improve age-related muscle loss by increasing muscle mass or inhibiting a reduction in muscle strength (see Experimental Example 1).

According to another embodiment of the present invention, D-ribo-2-hexulose increases the expression of IGF-1 serving as an upstream factor of protein expression in muscle tissue, inhibits the expression of myostatin, serving as an upstream factor of protein degradation, increases the expression of myogenic transcription factor genes Myf5, Myf6, and myogenin, and increases the protein levels of Akt, AMPK, PI3K, mTOR, PGC1-α, and their phosphorylated variants to increase the expression of muscle enhancement factor proteins (see Experimental Example 2).

According to still another embodiment of the present invention, it was confirmed that D-ribo-2-hexulose up-regulates the genes CISH and CerS1 associated with oxidative phosphorylation in gastrocnemius tissue, and down-regulates adiponectin, adipsin, CIDEC, haptoglobin, neuronatin, and SCD1 (see Experimental Example 3).

According to yet another embodiment of the present invention, it was confirmed that D-ribo-2-hexulose increases the ratio of muscle weight to fat weight (see Experimental Example 4).

According to yet another embodiment of the present invention, it was confirmed that D-ribo-2-hexulose activates an antioxidant system, reduces blood sugar, and decreases testosterone and cortisol levels (see Experimental Example 5).

Therefore, in the present invention, the D-ribo-2-hexulose may be characterized by satisfying one or more of the following characteristics, but the present invention is not limited thereto:

a) increasing the expression of insulin-like growth factor 1 (IGF-1);

b) inhibiting myostatin expression;

c) inhibiting a reduction in muscle strength; or d) increasing muscle mass.

In this specification, "insulin-like growth factor 1 (IGF-1)" is a naturally occurring polypeptide protein hormone that is known to play an important role in promoting growth in adolescents and play an important role in generating and repairing muscle tissue in adults.

According to one embodiment of the present invention, the D-ribo-2-hexulose may prevent, alleviate or treat sarcopenia because it may activate AMPK by inhibiting the expression of SCD1, the activated AMPK may increase the expression of PGC1-α and IGF-1, and the IGF-1 whose expression is increased may activate the PI3K/Akt pathway, which is a major signaling pathway for muscle hypertrophy, and the mTOR pathway for protein translation to increase protein synthesis and muscle production.

In this specification, "myostatin" is a protein that regulates muscle growth and belongs to the transforming growth factor (TGF)-beta group, and is known to have an effect of inhibiting the growth of skeletal muscle.

According to one embodiment of the present invention, the D-ribo-2-hexulose may more fundamentally prevent, ameliorate, or treat muscle loss and a reduction in muscle strength because it may inhibit NF-κB expression to reduce the expression of myostatin, which inhibits the growth of skeletal muscle, and reduce the expression of TNF-α, which stimulates muscle atrophy.

In this specification, the term "increasing muscle strength" or "inhibiting a reduction in muscle strength" refers to a phenomenon in which overall muscle strength increases due to an increase in skeletal muscle mass or an improvement in muscular function, and does not refer to an effect limited to a group of patients with a specific disease.

In the present specification, the term "increase in muscle mass" refers to an action of improving the growth of muscle among the body components. In this case, muscle mass may be increased through physical exercise and endurance improvement, and may also be increased by administering a substance having a muscle growth effect into the body. The type of muscle is not limited.

In the present specification, the term "active ingredient" refers to a component that may exhibit the desired activity alone or exhibit the desired activity together with a carrier having no activity itself.

In the present invention, the term "pharmaceutical composition" refers to a composition prepared for the purpose of preventing or treating a disease, and may be formulated and used in various forms according to conventional methods. For example, the pharmaceutical composition may be formulated into oral formulations such as powders, granules, tablets, capsules, suspensions, emulsions, syrups, and the like, and may also be formulated and used in the form of external preparations, suppositories and sterile injection solutions.

The pharmaceutical composition according to the present invention may further include suitable carriers, excipients and diluents commonly used in the manufacture of pharmaceutical compositions. For example, the excipient may include one or more selected from the group consisting of a diluent, a binder, a disintegrant, a lubricant, an adsorbent, a moisturizer, a film-coating material, and a controlled-release additive.

The pharmaceutical compositions according to the present invention may be formulated and used in the form of external preparations, such as powders, granules, sustained-release granules, enteric granules, solutions, eye drops, elixirs, emulsions, suspensions, spirits, troches, perfumes, limonades, tablets, sustained-release tablets, enteric tablets, sublingual tablets, hard capsules, soft capsules, sustained-release capsules, enteric capsules, pills, tinctures, soft extracts, dry extracts, fluid extracts, injections, capsules, perfusates, plasters, lotions, pastes, sprays, inhalants, patches, sterile injection solutions, aerosols, or the like, according to conventional methods. Also, the external preparations may have a formulation such as a cream, a gel, a patch, a spray, an ointment, a plaster, a lotion, a liniment, a paste, a cataplasma, or the like.

The carriers, excipients, and diluents that may be included in the pharmaceutical composition according to the present invention include lactose, dextrose, sucrose, oligosaccharides, sorbitol, mannitol, xylitol, erythritol, maltitol, starch, acacia gum, alginate, gelatin, calcium phosphate, calcium silicate, cellulose, methyl cellulose, microcrystalline cellulose, polyvinyl pyrrolidone, water, methylhydroxybenzoate, propylhydroxybenzoate, talc, magnesium stearate, and mineral oil.

When formulated, the pharmaceutical composition is prepared using commonly used diluents or excipients such as fillers, extenders, binders, wetting agents, disintegrants, surfactants, and the like.

As the additives for tablets, powders, granules, capsules, pills, and troches according to the present invention, excipients such as corn starch, potato starch, wheat starch, lactose, sucrose, glucose, fructose, di-mannitol, precipitated calcium carbonate, synthetic aluminum silicate, calcium monohydrogen phosphate, calcium sulfate, sodium chloride, sodium bicarbonate, purified lanolin, microcrystalline cellulose, dextrin, sodium alginate, methyl cellulose, sodium carboxymethyl cellulose, kaolin, urea, colloidal silica gel, hydroxypropyl starch, hydroxypropylmethyl cellulose (HPMC) 1928, HPMC 2208, HPMC 2906, HPMC 2910, propylene glycol, casein, calcium lactate, Primogel, and the like; binders such as gelatin, gum arabic, ethanol, agar powder, cellulose acetate phthalate, carboxymethyl cellulose, calcium carboxymethyl cellulose, glucose, purified water, sodium caseinate, glycerin, stearic acid, sodium carboxymethyl cellulose, sodium methyl cellulose, methyl cellulose, microcrystalline cellulose, dextrin, hydroxycellulose, hydroxypropyl starch, hydroxymethyl cellulose, purified shellac, gelatinized starch, hydroxypropyl cellulose, hydroxypropyl methyl cellulose, polyvinyl alcohol, polyvinyl pyrrolidone, and the like may be used. Also, disintegrants such as hydroxypropyl methyl cellulose, corn starch, agar powder, methyl cellulose, bentonite, hydroxypropyl starch, sodium carboxymethyl cellulose, sodium alginate, calcium carboxymethyl cellulose, calcium citrate, sodium lauryl sulfate, silicic anhydrides, 1-hydroxy propyl cellulose, dextran, ion exchange resins, polyvinyl acetate, formaldehyde-treated casein and gelatin, alginic acid, amylose, guar gum, sodium hydrogen carbonate, polyvinyl pyrrolidone, calcium phosphate, gelatinized starch, gum arabic, amylopectin, pectin, sodium polyphosphate, ethyl cellulose, sucrose, magnesium aluminum silicate, a di-sorbitol solution, silicic anhydrides, and the like; lubricants such as calcium stearate, magnesium stearate, stearic acid, hydrogenated vegetable oil, talc, lycopodium, kaolin, petrolatum, sodium stearate, cacao butter, sodium salicylate, magnesium salicylate, polyethylene glycol (PEG) 4000, PEG 6000, liquid paraffin, hydrogenated soybean oil (Lubri wax), aluminum stearate, zinc stearate, sodium lauryl sulfate, magnesium oxide, Macrogol, synthetic aluminum silicate, silicic anhydrides, higher fatty acids, higher alcohols, silicone oil, paraffin oil, polyethylene glycol fatty acid ethers, starch, sodium chloride, sodium acetate, sodium oleate, dl-leucine, light silicic anhydrides, and the like may be used.

As the additives for liquid preparations according to the present invention, water, dilute hydrochloric acid, dilute sulfuric acid, sodium citrate, sucrose monostearate, polyoxyethylene sorbitol fatty acid esters (Tween esters), polyoxyethylene monoalkyl ethers, lanolin ethers, lanolin esters, acetic acid, hydrochloric acid, aqueous ammonia, ammonium carbonate, potassium hydroxide, sodium hydroxide, prolamine, polyvinyl pyrrolidone, ethyl cellulose, sodium carboxymethyl cellulose, and the like may be used.

In the syrup according to the present invention, a solution of sucrose, other sugars, or a sweetener may be used. When necessary, aromatics, coloring agents, preservatives, stabilizing agents, suspending agents, emulsifying agents, thickeners, and the like may be used.

Purified water may be used in the emulsion according to the present invention, and emulsifying agents, preservatives, stabilizing agents, fragrances, and the like may be used when necessary.

As the suspending agent according to the present invention, suspending agents such as acacia, tragacantha, methyl cellulose, carboxymethyl cellulose, sodium carboxymethyl cellulose, microcrystalline cellulose, sodium alginate, hydroxypropyl methyl cellulose (HPMC), HPMC 1828, HPMC 2906, HPMC 2910, and the like may be used. When necessary, surfactants, preservatives, stabilizing agents, coloring agents, and fragrances may be used.

The injections according to the present invention may include solvents such as distilled water for injection, a 0.9% sodium chloride injection, a dextrose injection, a dextrose+ sodium chloride injection, PEG, lactated Ringer's solution, ethanol, propylene glycol, non-volatile sesame oil, cottonseed oil, peanut oil, soybean oil, corn oil, ethyl oleate, isopropyl myristate, benzene benzoate, and the like; solubilizing aids such as sodium benzoate, sodium salicylate, sodium acetate, urea, urethane, monoethylacetamide, butazolidine, propylene glycol, Tweens, nicotinamide, hexamine, dimethylacetamide, and the like; buffers such as weak acids and salts thereof (acetic acid and sodium acetate), weak bases and salts thereof (ammonia and ammonium acetate), organic compounds, proteins, albumin, peptones, gums, and the like; isotonic agents such as sodium chloride; stabilizing agents such as sodium bisulfite ($NaHSO_3$), carbon dioxide gas, sodium metabisulfite ($Na_2S_2O_5$), sodium sulfite ($Na_2SO_3$), nitrogen gas ($N_2$), ethylene diamine tetraacetic acid, and the like; antioxidants such as 0.1% sodium bisulfide, sodium formaldehyde sulfoxylate, thiourea, ethylene diamine disodium tetraacetate, acetone sodium bisulfite, and the like; analgesics such as benzyl alcohol, chlorobutanol, procaine hydrochloride, glucose, calcium gluconate, and the like; and suspending agents such as CMC sodium, sodium alginate, Tween 80, aluminum monostearate, and the like.

As the suppository according to the present invention, cacao butter, lanolin, Witepsol, polyethylene glycol, glycerogelatin, methyl cellulose, carboxymethyl cellulose, a mixture of stearic acid and oleic acid, Subanal, cottonseed oil, peanut oil, palm oil, cacao butter+cholesterol, Lecithin, Lanette Wax, glycerol monostearate, Tween or Span, Imhausen, monolene (propylene glycol monostearate), glycerin, Adeps solidus, Buytyrum Tego-G, Cebes Pharma 16, Hexalide Base 95, Cotomar, Hydrokote SP, S-70-XXA, S-70-XX75 (S-70-XX95), Hydrokote 25, Hydrokote 711, Idropostal, Massa estrarium (A, AS, B, C, D, E, I, T), Massa-MF, Marsupol, Marsupol-15, Neosupostal-N, Paramound-B, Suposiro (OSI, OSIX, A, B, C, D, H, L), suppository type IV (AB, B, A, BC, BBG, E, BGF, C, D, 299), Supostal (N, Es), Wecobi (W, R, S, M, Fs), Tegester triglyceride bases (TG-95, MA, 57), and the like may be used.

Examples of solid formulations for oral administration include tablets, pills, powders, granules, capsules, and the like, and such solid formulations may be prepared by mixing an extract with at least one excipient such as starch, calcium carbonate, sucrose or lactose, gelatin, and the like. In addition to simple excipients, lubricants such as magnesium stearate and talc may also be used.

Examples of liquid formulations for oral administration include suspensions, internal solutions, emulsions, syrups, and the like. In this case, various excipients such as wetting agents, sweeteners, flavoring agents, preservatives, and the like may be included in addition to commonly used simple diluents such as water and liquid paraffin. Examples of formulations for parenteral administration may include sterile aqueous solutions, non-aqueous solvents, suspensions, emulsions, freeze-dried formulations, and suppositories. Propylene glycol, polyethylene glycol, vegetable oils such as olive oil, injectable esters such as ethyl oleate, and the like may be used as the non-aqueous solvents and suspending agents.

The pharmaceutical composition according to the present invention may be administered in a pharmaceutically effective amount. In the present invention, the "pharmaceutically effective amount" refers to an amount sufficient to treat a disease with a reasonable benefit/risk ratio applicable to medical treatment, and a level of the effective amount may be determined according to the type of a patient's disease, the severity of the disease, the activity of a drug, the sensitivity to the drug, the time of administration, the route of administration, and the excretion rate, the duration of treatment, factors including drugs used concurrently, and other factors well known in the medical field.

The pharmaceutical composition according to the present invention may be administered as an individual therapeutic agent or in combination with other therapeutic agents, and may be administered sequentially or concurrently with a conventional therapeutic agent and may be administered once or multiple times. It is important to administer the pharmaceutical composition according to the present invention in an amount sufficient to obtain the maximum effect with the minimum amount without side effects in consideration of all the above-mentioned factors, and such an amount may be easily determined by a person having ordinary skill in the technical field to which the present invention pertains.

The pharmaceutical composition according to the present invention may be administered to a subject through various routes of administration. All modes of administration may be expected, and may, for example, include oral administration, subcutaneous injection, intraperitoneal administration, intravenous injection, intramuscular injection, injection into the paraspinal space (intrathecal), sublingual administration, buccal administration, rectal insertion, vaginal insertion, intraocular administration, auricular administration, intranasal administration, inhalation, spraying through the mouth or nose, intradermal administration, transdermal administration, and the like.

The pharmaceutical composition of the present invention may be determined according to the type of drug as an active ingredient together with various related factors such as the type of disease to be treated, the route of administration, the age, gender, and weight of a patient, the severity of a disease, and the like.

Also, the present invention provides a method of preventing or treating sarcopenia, which includes: administering the composition comprising D-ribo-2-hexulose as an active ingredient to a subject in need thereof.

In addition, the present invention provides a use of the composition comprising D-ribo-2-hexulose as an active ingredient for the prevention or treatment of sarcopenia.

Additionally, the present invention provides a use of D-ribo-2-hexulose for the manufacture of a drug for the treatment of sarcopenia.

In the present invention, the term "subject" refers to a subject in need of treatment of a disease, and, more specifically, a mammal such as a human or non-human primate, a mouse, a rat, a dog, a cat, a horse, a cow, and the like.

In the present invention, the term "administration" refers to an action of providing a predetermined composition of the present invention to a subject using any suitable method.

In the present invention, the term "prevention" refers to all actions of suppressing or delaying the onset of a target disease, the term "treatment" refers to all actions of improving or beneficially changing the target disease and the resulting metabolic abnormalities through the administration of the pharmaceutical composition according to the present invention, and the term "alleviation" refers to all actions of reducing parameters associated with the target disease, for example, the severity of a symptom, through the administration of the composition according to the present invention.

Further, the present invention provides a food composition for preventing or alleviating sarcopenia, which comprises D-ribo-2-hexulose as an active ingredient.

When the D-ribo-2-hexulose of the present invention is used as a food additive, the D-ribo-2-hexulose may be added as it is, or used together with other foods or food ingredients. In this case, the D-ribo-2-hexulose of the present invention may be used appropriately according to conventional methods. The mixing amount of the active ingredient may be appropriately determined according to the purpose of use (prevention, health or therapeutic treatment). In general, when foods or beverages are prepared, the D-ribo-2-hexulose of the present invention may be added in an amount of 15% by weight or less, or 10% by weight or less based on the total weight of the raw material. However, in the case of long-term intake for the purpose of health and hygiene or for the purpose of health control, the amount may be less than the above range. Because the active ingredient has no problems in terms of safety, the active ingredient may be used in an amount greater than the above range.

There is no particular limitation on the type of food. Examples of foods to which the above substance may be added may include meat, sausage, bread, chocolate, candies, snacks, confectioneries, pizza, ramen, other noodles, gum, dairy products including ice cream, various soups, beverages, tea, drinks, alcoholic beverages, vitamin complexes, and the like, and may include all of health functional foods in the usual sense.

The health beverage composition according to the present invention may contain various flavoring agents, natural carbohydrates, and the like as additional components, as in conventional beverages. The above-described natural carbohydrates may include monosaccharides such as glucose and fructose, disaccharides such as maltose and sucrose, polysaccharides such as dextrins and cyclodextrins, and sugar alcohols such as xylitol, sorbitol, and erythritol. As sweeteners, natural sweeteners such as thaumatin and *stevia* extracts, synthetic sweeteners such as saccharin and aspartame, and the like may be used. The proportion of the natural carbohydrates per 100 mL of the composition of the present invention may be generally in a range of approximately 0.01 to 0.20 g, or 0.04 to 0.10 g.

In addition to the above-described substances, the composition of the present invention may contain various nutrients, vitamins, electrolytes, flavors, colorants, pectic acid and salts thereof, alginic acid and salts thereof, organic acids, protective colloidal thickeners, pH adjusters, stabilizing agents, preservatives, glycerin, alcohol, carbonating agents used for carbonated beverages, and the like. In addition, the composition of the present invention may contain fruit flesh for preparing natural fruit juice, fruit juice beverages, and vegetable beverages. These ingredients may be used individually or in combination. The proportion of these additives is not critical, but may generally be in a range of 0.01 to 0.20 parts by weight based on 100 parts by weight of the composition of the present invention In the present invention, the food composition may be a health functional food composition, but the present invention is not limited thereto.

In this specification, the term "health functional food" is the same term as a food for special health use (FoSHU), and refers to a processed food with high medicinal and medical effects to efficiently exhibit bioregulatory functions in addition to nutrient supply. In this case, the food may be prepared in various forms such as tablets, capsules, powders, granules, liquids, pills, and the like in order to obtain useful effects for preventing or improving sarcopenia.

The health functional food of the present invention may be prepared by a method commonly used in the art, and may be prepared by adding raw materials and components commonly added in the art during the preparation. Also, unlike general drugs, the health functional food of the present invention has an advantage in that it has no side effects that may occur when taking a drug for a long time because food is used as a raw material, and may have excellent portability.

MODE FOR INVENTION

Hereinafter, preferred examples of the present invention are provided to aid in understanding the present invention. However, it should be understood that the following examples are provided only for the purpose of understanding the present invention more easily and are not intended to limit the contents of the present invention.

EXAMPLES

Example 1: Breeding and Diet of Laboratory Animals

Twenty-one 48-week-old C57BL/6J male mice and seven 8-week-old C57BL/6J male mice were purchased from JA BIO Inc. (Korea). The purchased animals were raised in a breeding room with a controlled temperature (20 to 23° C.) and a light/dark cycle (a 12-hour cycle), and were provided with pelletized commercial non-purified feed for the first week.

The 48-week-old aged mice were randomly divided into two groups and supplied with each experimental diet shown in the following Table 1 for 12 weeks. Specifically, a negative control group (NC, n=7, American Institute of Nutrition AIN-93G Semisynthetic diet); a D-ribo-2-hexulose-treated group (D-ribo-2-hexulose; DRH, n=7; a portion of cellulose in AIN-93G was replaced with 3% D-ribo-2-hexulose). As shown in Table 1 below, AIN-93G was provided to a young mouse control group (YC; 8 weeks old) from the week 8 of the experiment until the end of the experiment. The dose of D-ribo-2-hexulose was set at 3% based on previous animal studies. In the previous studies, the dose of D-ribo-2-hexulose was determined to be 3% in order to investigate a biological effect at a lower dose than the dose. During the experiment, the mice had free access to distilled water, and the food intakes and body weights of the mice were measured weekly, and blood glucose was measured once every 4 weeks. All animal experiments were approved by the Animal Research Ethics Committee of KyungPook National University (Approval Number: KNU-2020-109).

TABLE 1

| Ingredients (g) | AIN-93G | AIN-93G + 3% DRH |
| --- | --- | --- |
| Casein | 200 | 200 |
| Corn Starch | 397.5 | 397.5 |
| Sucrose | 100 | 100 |
| Maltodextrin | 132 | 132 |
| Cellulose | 50 | 20 |
| Soybean Oil | 70 | 70 |
| Mineral Mix | 35 | 35 |
| Vitamin Mix | 10 | 10 |
| TBHQ, antioxidant | 0.014 | 0.014 |
| L-Cystine | 3 | 3 |
| Cholin Bitartrate | 2.5 | 2.5 |
| D-ribo-2-hexulose | — | 30 |
| Total (g) | 1,000 | 1,000 |
| Calorie (Kcal/g) | 3,948 | 3,948 |

Example 2: Whole-Body Tension and Left Hind Leg Thickness

The whole-body tension was measured and evaluated using a digital force gauge (Korea, JM Instruments Corp., FGJN.FGP Series). For each mouse, the whole-body tension was measured and evaluated at intervals of 5 days. In order to evaluate the whole-body tension on week 10 of the experiment, the average value of the maximum whole-body tension was calculated as force per body weight ($Ng^{-1}$ BW).

The thicknesses of left hind legs were measured using Bluetec digital calipers (Korea, BLUETEC, BD500) every 4 weeks during the experiment period, and the leg thickness was divided by the body weight of each mouse in order to minimize differences between individuals (mm/100 g× body weight).

Example 3: Biochemical Profiles of Plasma, Liver, and Muscle Tissue

Plasma TG and TC analysis was performed using an enzyme kit (Asan Pharmaceutical Co., Ltd., Korea). Free fatty acid (FFA) was also measured using an enzyme kit (Abcam., USA). Liver and muscle lipids were extracted, and the dried lipid residue was then dissolved in 1 mL of ethanol for the measurement of TG, TC, and FFA. For emulsification, Triton X-100 and a sodium cholate solution were added to 200 μL of the dissolved lipid solution. The TG, TC, and FFA were analyzed in the same kit as the enzyme kit used for plasma lipid analysis.

For cytokine analysis, plasma cytokines (TNF-α, IL-1β, and IL-4) were measured with a Merck Millipore product (MCYTOMAG-70K, Merck, USA). Plasma (30 μL) from each mouse was analyzed in duplicate. Hormone analysis was performed using a cortisol and testosterone parameter assay kit (R&D Systems, USA).

To analyze antioxidant activity, superoxide dismutase (SOD) activity was measured in an alkaline state by pyrogallol autoxidation using a modified method of Marklund et al. Also, catalase (CAT) activity was measured using a modified method of Aebi et al. Paraoxonase (PON) activity was measured using a modified method of Mackness et al. in order to measure an increase in absorbance of p-nitrophenol. Glutathione reductase (GR) activity was measured using a modified method of Pinto and Bartley, which was used to measure NADPH oxidation. Total glutathione (GSH) content was measured using a modified method of Ellman et al.

Example 4: Histopathology and Immunohistochemistry (IHC) Analysis

For morphological tissue observation, parts of liver and muscle tissues were fixed with a 10% formaldehyde solution for 24 hours. Thereafter, the samples were subjected to replacement with the same solution twice, dehydrated twice with ethanol, embedded in paraffin, and treated with poly-L-lysine to prepare tissue slices having a thickness of 5 μm. For morphological analysis, among the prepared tissue sections, the liver tissue was stained with H&E and MT, and the muscle tissue was stained with H&E and Sirius red, and magnified 200 times under an optical microscope. For IHC analysis, the muscle tissue was stained with IGF-1 and Myostatin, and then observed under an optical microscope.

Example 5: mRNA Sequencing

Sequences were filtered, and low-quality reads were discarded from the data set (including reads consisting of more than 10% ambiguous (N) bases, reads having more than 40% bases with a phred quality score of less than 20, and reads having an average phred quality score of less than 20 (Trimmomatic 0.38)) according to the parameters. The resulting high-quality reads were mapped to the human reference genome (StringTie version 2.1.3b) using Aligner software STAR, v.2.6.0c.

Example 6: Real-Time PCR

After total RNA was isolated, total complementary DNA (cDNA) was synthesized. For real-time PCR analysis, template cDNA was diluted with RNAse-free water and used at a concentration of 25 ng/μL. Then, gene expression was analyzed using a QuantitTeck SYBR Green PCR kit (QIA-GEN, Germany). Primers capable of analyzing the expression of each gene were synthesized, as shown in Table 2 below, by commissioning Genotech Co., Ltd. (Korea, Daejeon).

TABLE 2

| Gene ID | Direction | Sequence (5'→3') |
|---|---|---|
| GAPDH (14433) | Forward | TGC AGT GGC AAA GTG GAG AT (SEQ ID NO: 1) |
| | Reverse | TTG AAT TTG CCG TGA GTG GA (SEQ ID NO: 2) |
| Atrogin-1 (67731) | Forward | AAC CGG GAG GCC AGC TAA AGA ACA (SEQ ID NO: 3) |
| | Reverse | TGG GCC TAC AGA ACA GAC AGT GC (SEQ ID NO: 4) |
| FoxO3 (56484) | Forward | TCG CCT CCT GGC GGG CTT A (SEQ ID NO: 5) |
| | Reverse | ACG GCG GTG CTA GCC TGA GA (SEQ ID NO: 6) |
| Mef2 (17260) | Forward | ACA CGC ATA ATG GAT GAG AGG AAC CGA C (SEQ ID NO: 7) |
| | Reverse | CAA CGA TAT CCG AGT TCG TCC TGC TTT C (SEQ ID NO: 8) |
| Myf5 (17877) | Forward | AGG AAA AGA AGC CCT GAA GC (SEQ ID NO: 9) |
| | Reverse | GCA AAA AGA ACA GGC AGA GG (SEQ ID NO: 10) |
| Myf6 (17878) | Forward | CAA GAA AAT CTT GAG GGT GCG G (SEQ ID NO: 11) |
| | Reverse | TTA GCC GTT ATC ACG AGC CC (SEQ ID NO: 12) |
| MyoD (17927) | Forward | GCT TCT ATC GCC GCC ACT CC (SEQ ID NO: 13) |
| | Reverse | CGC ACA TGC TCA TCC TCA CG (SEQ ID NO: 14) |
| Myogenin (17928) | Forward | CCT TGC TCA GCT CCC TCA (SEQ ID NO: 15) |
| | Reverse | TGG GAG TTG CAT TCA CTG G (SEQ ID NO: 16) |
| MuRF1 (4433766) | Forward | GAG AAC CTG GAG AAG CAG CT (SEQ ID NO: 17) |
| | Reverse | CCG CGG TTG GTC CAG TAG (SEQ ID NO: 18) |
| CerS1 (93898) | Forward | GCA GCC ACC ACA CAC AT (SEQ ID NO: 19) |
| | Reverse | ATG CCT GAC CTC CAG TCA TA (SEQ ID NO: 20) |
| CIDEC (14311) | Forward | TCC AGG ACA TCT TGA AAC TT (SEQ ID NO: 21) |
| | Reverse | GGC TTG CAA GTA TTC TTC TGT (SEQ ID NO: 22) |
| CISH (12700) | Forward | GGA CAT GGT CCT TTG CGT ACA G (SEQ ID NO: 23) |
| | Reverse | GGA GAA CGT CTT GGC TAT GCA C (SEQ ID NO: 24) |
| SCD1 (20249) | Forward | TCC TGC TCA TGT GCT TCA TC (SEQ ID NO: 25) |
| | Reverse | GGA TGT TCT CCC GAG ATT GA (SEQ ID NO: 26) |
| Adipsin (11537) | Forward | AAC CGG ACA ACC TGC AAT C (SEQ ID NO: 27) |
| | Reverse | CCC ACG TAA CCA CAC CTT C (SEQ ID NO: 28) |
| Adiponectin (11450) | Forward | CCG TTC AGC ATT CAG TGT (SEQ ID NO: 29) |
| | Reverse | CAG CCT TGT CCT TCT TGT A (SEQ ID NO: 30) |
| Haptoglobin (15439) | Forward | CTG TGG AGT TGG GCA ATG ATG (SEQ ID NO: 31) |
| | Reverse | AAC CAA GTG CTC CAC ATA GCC (SEQ ID NO: 32) |
| Neuronatin (18111) | Forward | GCT CAT CAT CGG CTG GTA CA (SEQ ID NO: 33) |
| | Reverse | CTT GGC AAG TGC TCC TCT GA (SEQ ID NO: 34) |

HiSeq Illumina sequencing was performed commercially using liver tissue (Macrogen, Korea). RNA-seq libraries were prepared from total RNA using a TruSeq Stranded mRNA sample preparation kit. The libraries were sequenced on an Illumina Nextseq 500 sequencer using paired-end runs (2×75 bases). The detailed protocol is provided by Illumina (https://sapac.illumina.com/).

Each of the reaction solutions consisted of 10 μL of SYBR Green, 2 μL of a template, and 200 μM primers. RNAse-free water was added to a final volume of 20 μL, and reacted at 94° C. for 15 seconds, and then 58° C. and 72° C. for 30 seconds. The reaction solution was reacted 40 times at 65° C. for 30 seconds at 15 seconds per cycle. In this case, by monitoring the fluorescence signal for each cycle and analyzing the resulting threshold cycle (Ct), mRNA expression between the respective experimental groups was quantitatively analyzed using a CFX96 Real-time system (Bio-Rad, USA). GAPDH (Gene ID 14433) was used as an internal transcriptional marker, and the gene primers used for amplification were as follows: MyoD (myoblast determination protein 1, Gene ID 17927), Myf5 (Gene ID 17877), Myf6 (Gene ID 17878), Myogenin (Gene ID 17928), Mef2 (Gene ID 17260), MuRF1 (Gene ID 4433766), Atrogin1 (Gene ID 67731), FoxO3 (Gene ID 56484), CerS1 (Gene ID 93898 (3)1), CIDEC1 (Gene ID 12700), SCD1 (Gene ID 20249), Adipsin (complement factor D, Gene ID 11537), Adiponectin (Gene ID 11450), Haptoglobin (Gene ID 15439), and Neuronatin (Gene ID 18111).

Example 7: Western Blotting

The amount of cytoplasmic and membrane proteins was quantified according to the Bradford method. Thereafter, a protein load was applied onto a 10% SDS-polyacrylamide gel, transferred to a Tris-glycine electrophoresis buffer for an hour, and then electrophoresed. The positions of the bands were confirmed using a Ponceau solution, blocking (5% skim milk in TBS/0.1% Tween-20) was performed at room temperature for 60 minutes in order to reduce non-specific reactions to the membrane. Then, the samples were reacted with a primary antibody overnight at 4° C.

Each of the antibodies was reacted with 5% skim milk diluted in the following ratios: Rabbit anti-mouse PGC1-α (1:1,000; Santa Cruz, USA), rabbit anti-mouse α-tubulin (1:1,000; Cell Signaling Technology, USA), rabbit anti-mouse p-Akt (1:1,000; Cell Signaling Technology, USA), rabbit anti-mouse Akt (1:1,000; Cell Signaling Technology, USA), rabbit anti-mouse p-PI3K (1:1,000; Cell Signaling Technology, USA), rabbit anti-mouse PI3K (1:1,000; Cell Signaling Technology), rabbit anti-mouse mTOR (1:1,000; Cell Signaling Technology, USA), rabbit anti-mouse TNF-α (1:1,000; Cell Signaling Technology, USA), rabbit anti-mouse adiponectin (1:1,000; Cell Signaling Technology, USA), rabbit anti-mouse haptoglobin (1:1,000; Abcam, USA), rabbit anti-mouse SCD1 (1:1,000; Cell Signaling Technology, USA), goat anti-mouse CerS1 (1:1,000; Novus Biologicals Ltd., USA), and rabbit anti-mouse NF-κB (1:000; Cell Signaling Technology, USA). The protein bands were washed, and the membrane was then reacted with a primary antibody in a TBST buffer (25 mM Tris-base, 155 mM NaCl, 0.1% Tween-20) in the presence of anti-rabbit IgG (1:1,000; Amersham Ltd., UK) or anti-goat IgG (1:1, 000; ABcam Inc., USA) secondary antibodies for 30 minutes, and reacted at room temperature for an hour. Then, the membrane was washed again with a TBST buffer for 30 minutes. Immunoreactive bands were developed on a film using an ECL kit (Pierce Chemical Co., IL) to check the bands in a final state.

Example 8: Blue Native Polyacrylamide Gel Electrophoresis (BN-PAGE) Analysis Mitochondria were isolated from the quadriceps muscle using the Potter-Elvehjem method. To extract respiratory SCs, a sample buffer cocktail was prepared using 8 μL of digitonin (Invitrogen, USA) per 50 μg of protein, 4×5 μL of a sample buffer (Invitrogen, USA) per 50 μg of protein, and 7 μL of water per 50 μg of protein. Thereafter, the solution was mixed with mitochondria. The BN-PAGE run and transfer were performed. An Ox-Phos Rodent WB antibody cocktail (Invitrogen, USA) was reacted at room temperature for 2 hours. Then, a secondary antibody solution Alk-Phos (Invitrogen, USA) was reacted at room temperature for an hour. Immunoreactive bands were developed using chromogen (BCIP/NBT). Then, the bands in a final state were checked.

Example 9: Statistical Analysis

Statistical analysis of all the experimental results was performed using a Statistical Package for Social Science (SPSS) package program. Data was expressed as mean±standard error (SE). Significant differences between the groups were confirmed through a Mann-Whitney U test. A value of $p<0.05$ was considered statistically significant.

EXPERIMENTAL EXAMPLES

Figures 1, 1A:
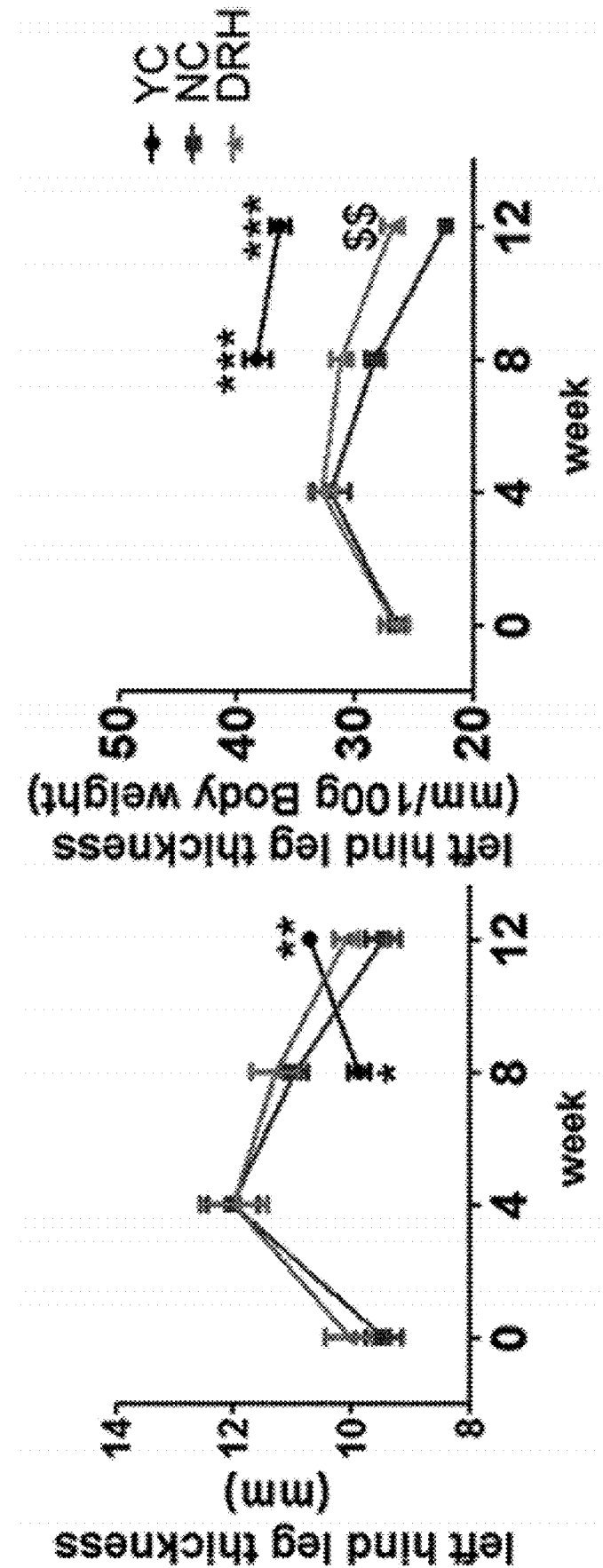
FIG. 1A is a diagram showing the results of measuring the thicknesses of the left hind legs of mice in a young mice control (YC) group, a negative control (NC) group, and a D-ribo-2-hexulose-supplemented (DRH) group.
Figures 1, 1B:
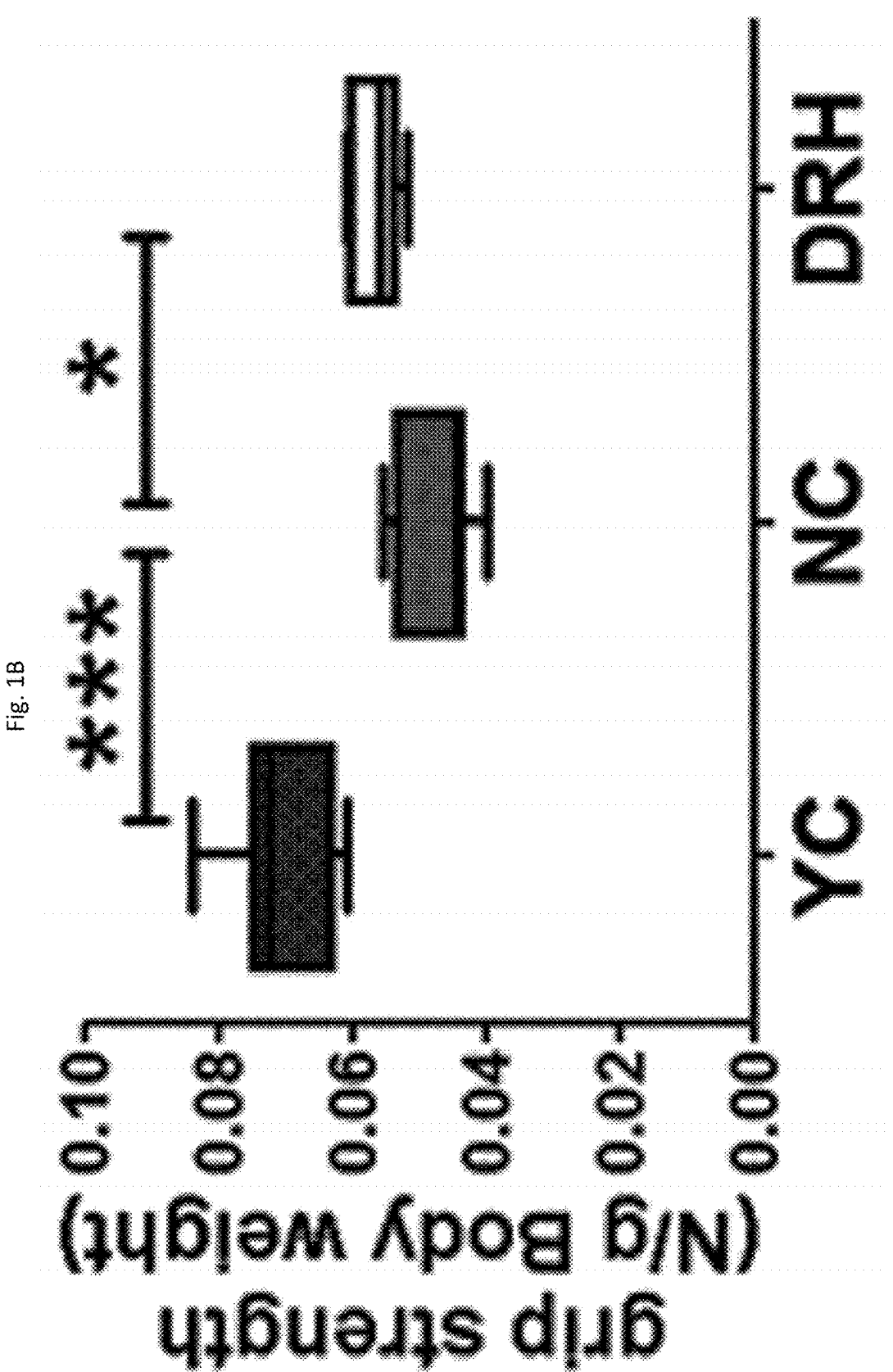
FIG. 1B is a diagram showing the results of measuring the whole-body tensions of mice in the YC, NC, and DRH groups.
Figures 1, 1C:
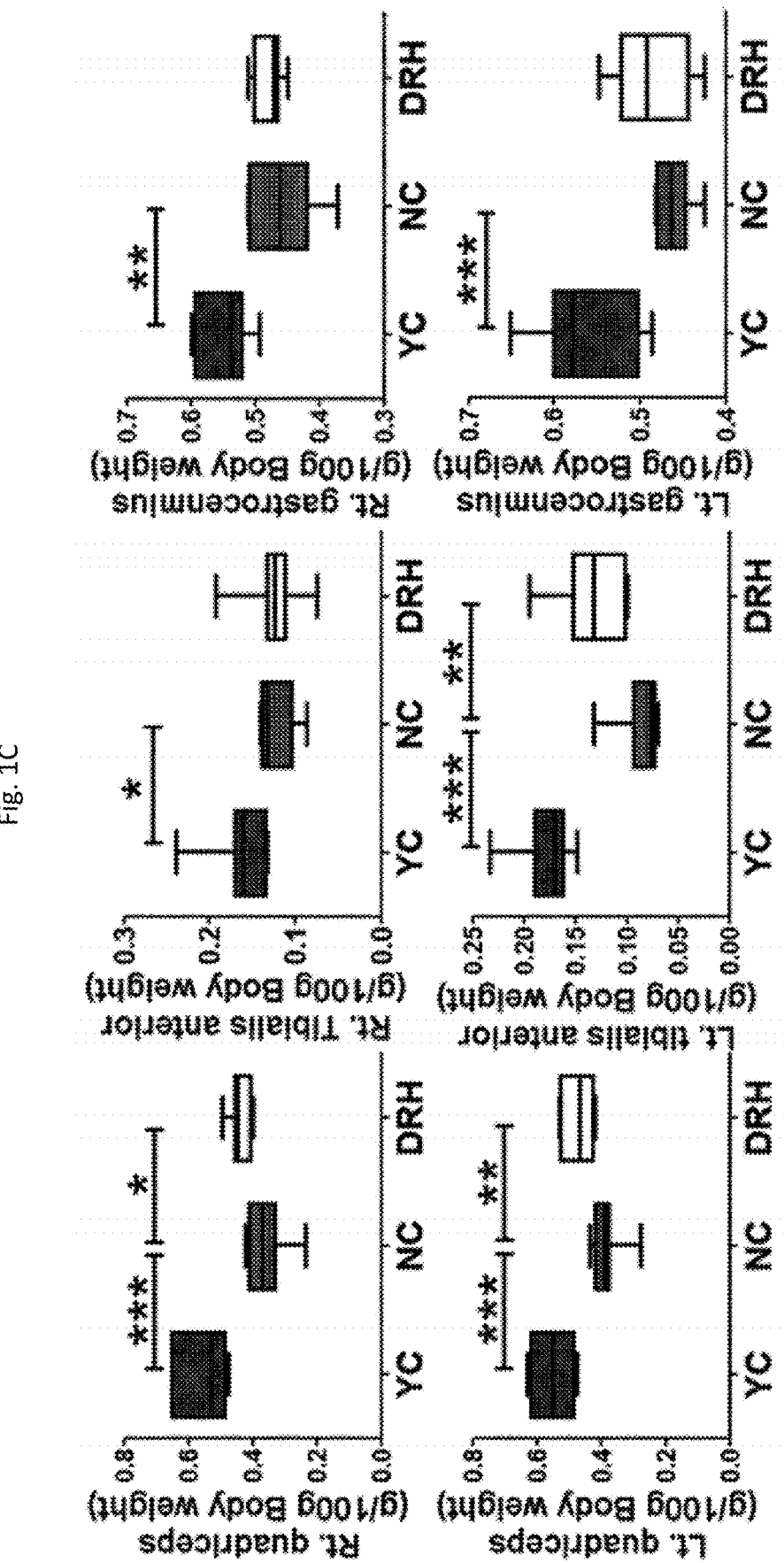
FIG. 1C is a diagram showing the results of measuring the weights of tissues of the quadriceps (left), anterior tibialis (middle), and gastrocnemius (right) of the mice in the YC, NC, and DRH groups. Here, the weight is based on 100 g of body weight.
Figures 1, 1D:
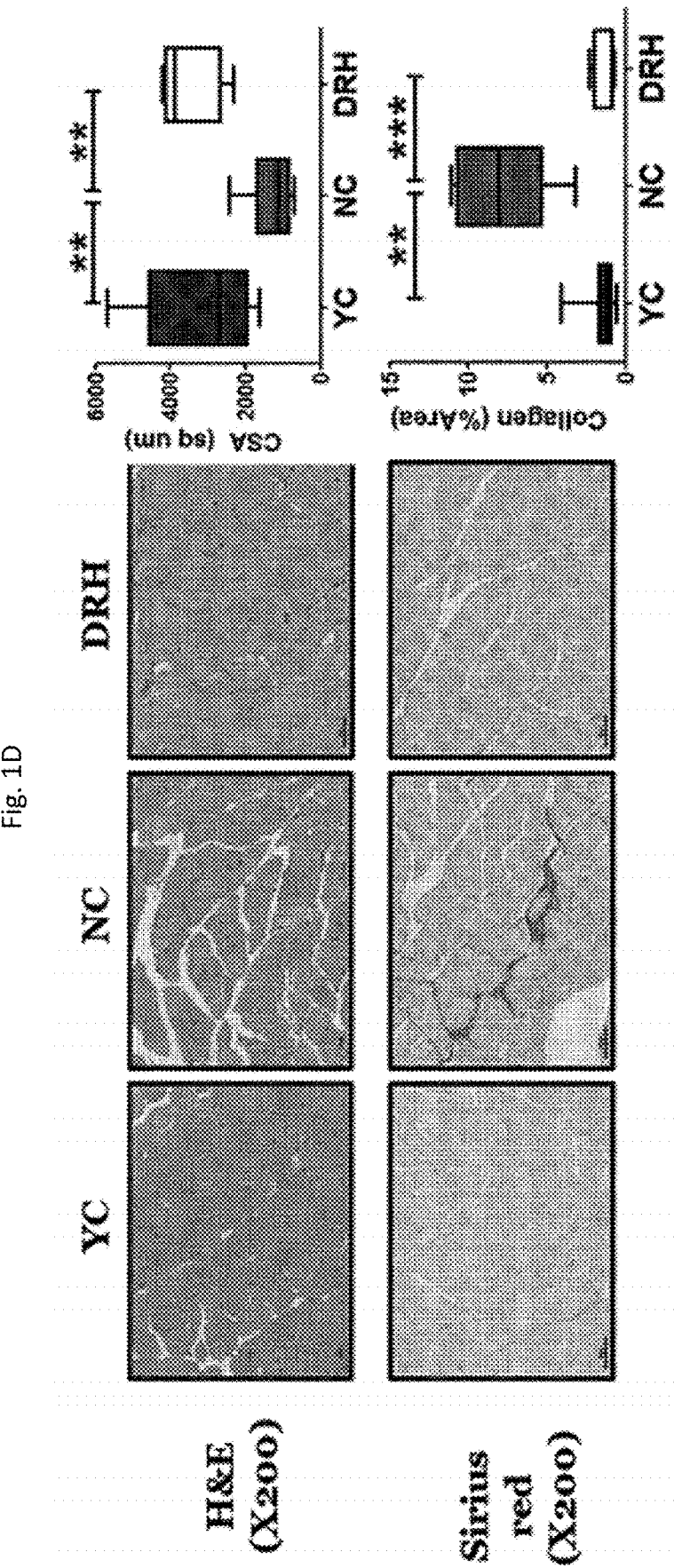
FIG. 1D is a diagram showing the results of H&E staining (upper left) and Sirius red staining (lower left) on the gastrocnemius tissues of the mice in the YC, NC, and DRH groups, and the results of measuring the muscle cross-sectional area (CSA; upper right) and the collagen area (lower right) of gastrocnemius tissue.

Experimental Example 1: D-Ribo-2-Hexulose Ameliorates Age-Related Muscle Loss As shown in Table 3 below, the final body weight and weight gain were significantly lower in the DRH group than in the NC group. The food intake was not significantly different between the NC and DRH groups. On the other hand, the food efficiency ratio (FER) significantly decreased in the DRH group compared to the NC group. In the case of the DRH group, the liver weight decreased and the kidney weight increased compared to the NC group. There was no significant difference in spleen weight. As shown in FIG. 1A, on week 12 of the experiment, the thicknesses of the left hind legs significantly increased in both the YC and DRH groups compared to the NC group. As shown in FIG. 1B, the whole-body tension significantly decreased in the NC group compared to the YC group. However, D-ribo-2-hexulose dramatically compensated for the decrease in the whole-body tension in the DRH group. The muscle weight significantly decreased in the NC group compared to the YC group. As shown in FIG. 1C, the weights of the right and left quadriceps and the left anterior tibialis significantly increased in the DRH group compared to the NC group. As shown in FIG. 1D, when morphological analysis was performed based on H&E (hematoxylin and eosin) staining of muscle tissue, the size of muscle fibers significantly increased in the YC group compared to the NC group.

Also, as shown in FIG. 1D, it can be seen that the reduction observed in the mice of the NC group was also improved in the mice of the DRH group, and that fibrosis progressed in the NC group compared to the YC group when the muscle tissue was analyzed through Sirius red staining. The progression of fibrosis in the DRH group was reduced to that of the YC group.

TABLE 3

|  | YC (Mean ± SD) | NC (Mean ± SD) | DRH (Mean ± SD) |
|---|---|---|---|
| Initial BW [g] | 24.71 ± 0.41*** | 36.35 ± 0.49 | 36.47 ± 0.53 |
| Final BW [g] | 30.77 ± 0.41*** | 43.44 ± 0.62 | 37.59 ± 0.56$^{\$\$}$ |
| Total BWG [g] | 5.71 ± 0.21 | 6.65 ± 0.45 | 1.36 ± 0.20$^{\$\$\$}$ |
| Food intake [g/day] | 3.10 ± 0.008* | 3.45 ± 0.05 | 3.46 ± 0.08 |

TABLE 3-continued

| | YC (Mean ± SD) | NC (Mean ± SD) | DRH (Mean ± SD) |
|---|---|---|---|
| Energy intake [g/day] | 12.21 ± 0.30* | 13.63 ± 0.22 | 13.23 ± 0.30 |
| FER | 0.04 ± 0.00 | 0.04 ± 0.00 | 0.00 ± 0.00$^{$$$}$ |
| Liver (g per 100 g BW) | 3.18 ± 0.05** | 3.88 ± 0.01 | 3.71 ± 0.07$^{$}$ |
| Kidney (g per 100 g BW) | 1.00 ± 0.01** | 0.89 ± 0.01 | 1.10 ± 0.02$^{$$}$ |
| Spleen (g per 100 g BW) | 0.20 ± 0.03 | 0.20 ± 0.00 | 0.20 ± 0.02 |

*$p < 0.05$,
**$p < 0.01$, and
***$p < 0.001$ represent significant differences between YC and NC groups;
$^{$}p < 0.05$,
$^{$$}p < 0.01$, and
$^{$$$}p < 0.001$ represent significant differences between DRH and NC groups,
BW: body weight, BWG: body weight gain, FER: food efficiency ratio = body weight gain/energy intake per day.

Figure 2:
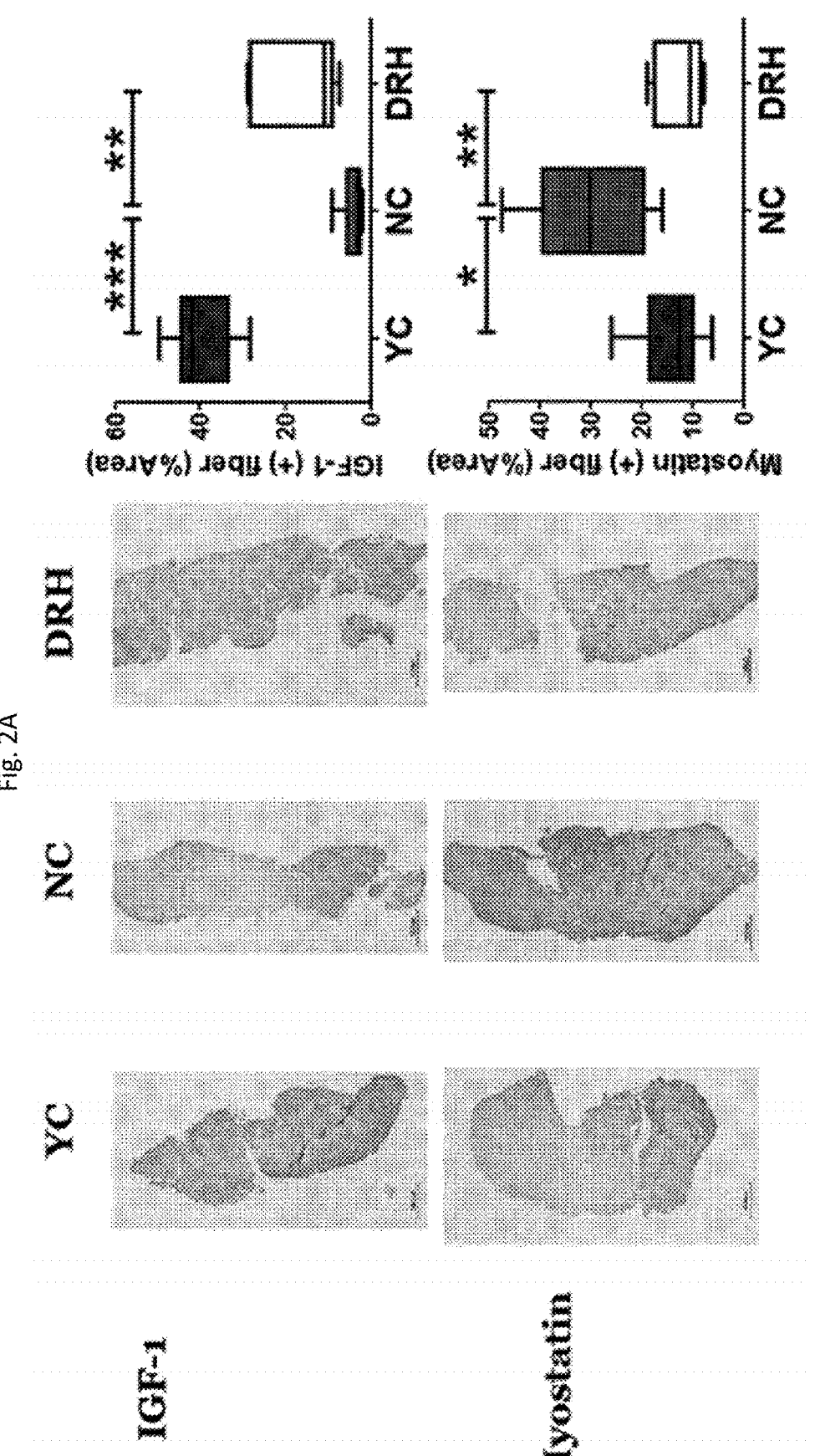
FIG. 2A is a diagram showing the results of confirming the expression of IGF-1 and myostatin in the mice of the YC, NC, and DRH groups through IHC analysis.
FIG. 2B is a diagram showing the results of confirming the expression of muscle strength-related genes (myoblast determination protein 1 (MyoD), myogenic factor 5 (Myf5), myogenic factor 6 (Myf6), myogenin, myocyte enhancer factor-2 (Mef2), muscle-specific RING-finger protein-1 (MuRF1), Atrogin 1, and forkhead box O3 (FoxO3) in the mice of the YC, NC, and DRH groups.
FIG. 2C is a diagram showing the results of measuring the protein levels of Akt, AMPK, PI3K, mTOR, PGC1-α, and their phosphorylated variants in the mice of the YC, NC, and DRH groups.

Experimental Example 2: D-Ribo-2-Hexulose Increases the Expression of Muscle Enhancement Factor Proteins As a result of IHC analysis, as shown in FIG. 2A, an expression level of insulin-like growth factor 1 (IGF-1), which is an upstream factor of protein synthesis, was significantly reduced in the NC group compared to the YC group, whereas supplementation with D-ribo-2-hexulose improved this reduction. An expression level of myostatin, which is an upstream factor of protein degradation in gastrocnemius muscle fibers, significantly increased in the NC group compared to the YC group. However, supplementation with D-ribo-2-hexulose suppressed this increase to the level of the YC group.

Figures 2, 2B:
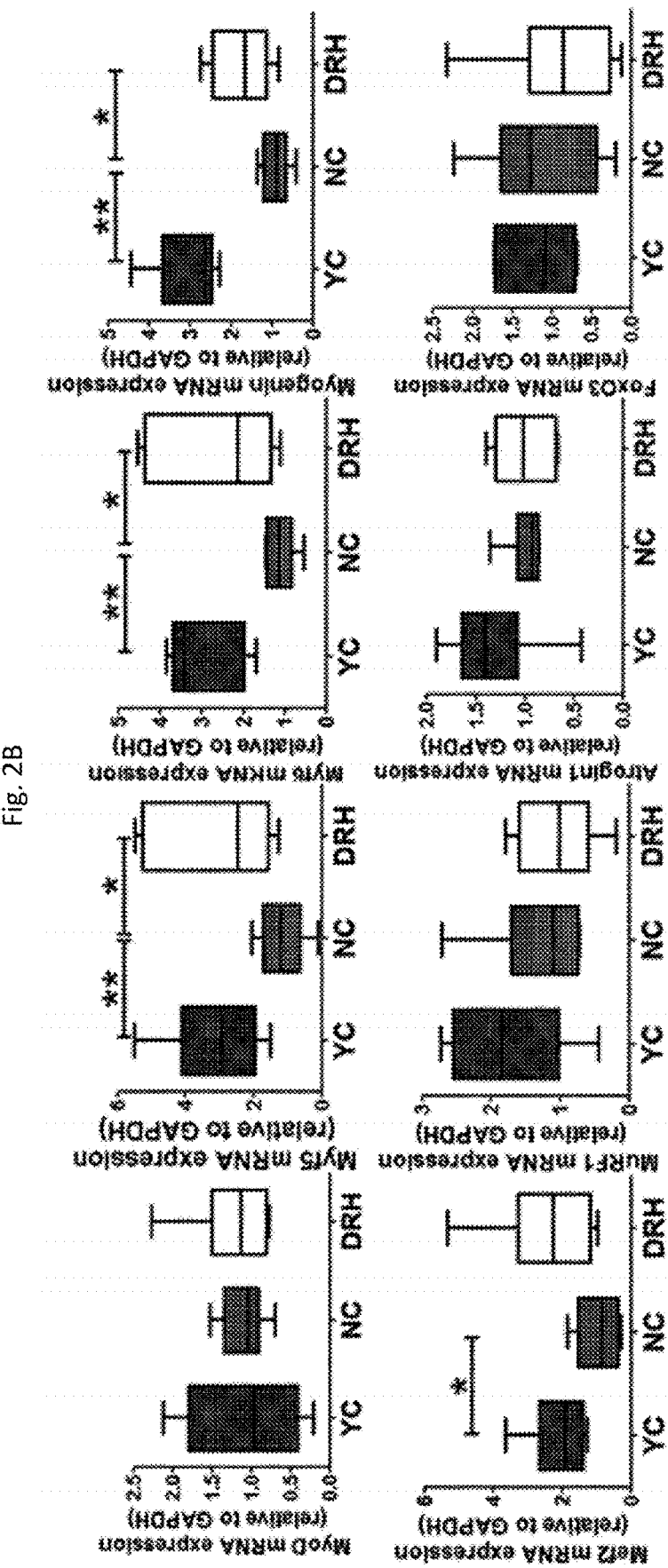

The expression of muscle strength-related genes was analyzed. As a result, as shown in FIG. 2B, there was no significant difference in the expression of protein degradation inhibitor genes (including a muscle cell apoptosis inhibitor gene MyoD), such as muscle-specific RING-finger protein-1 (MuRF1), Atrogin1, and Forkhead box O3 (FoxO3), in all three groups. However, the expression of myogenic transcription factor genes such as myogenic factor 5 (Myf5), myogenic factor 6 (Myf6), Myogenin, and myocyte enhancer factor-2 (Mef2) significantly decreased in the NC group compared to the YC group. This decrease was partially improved by supplementation with D-ribo-2-hexulose, especially in the expression of Myf5, Myf6, and Myogenin. There were significant differences between the NC and DRH groups.

Figures 2, 2C:
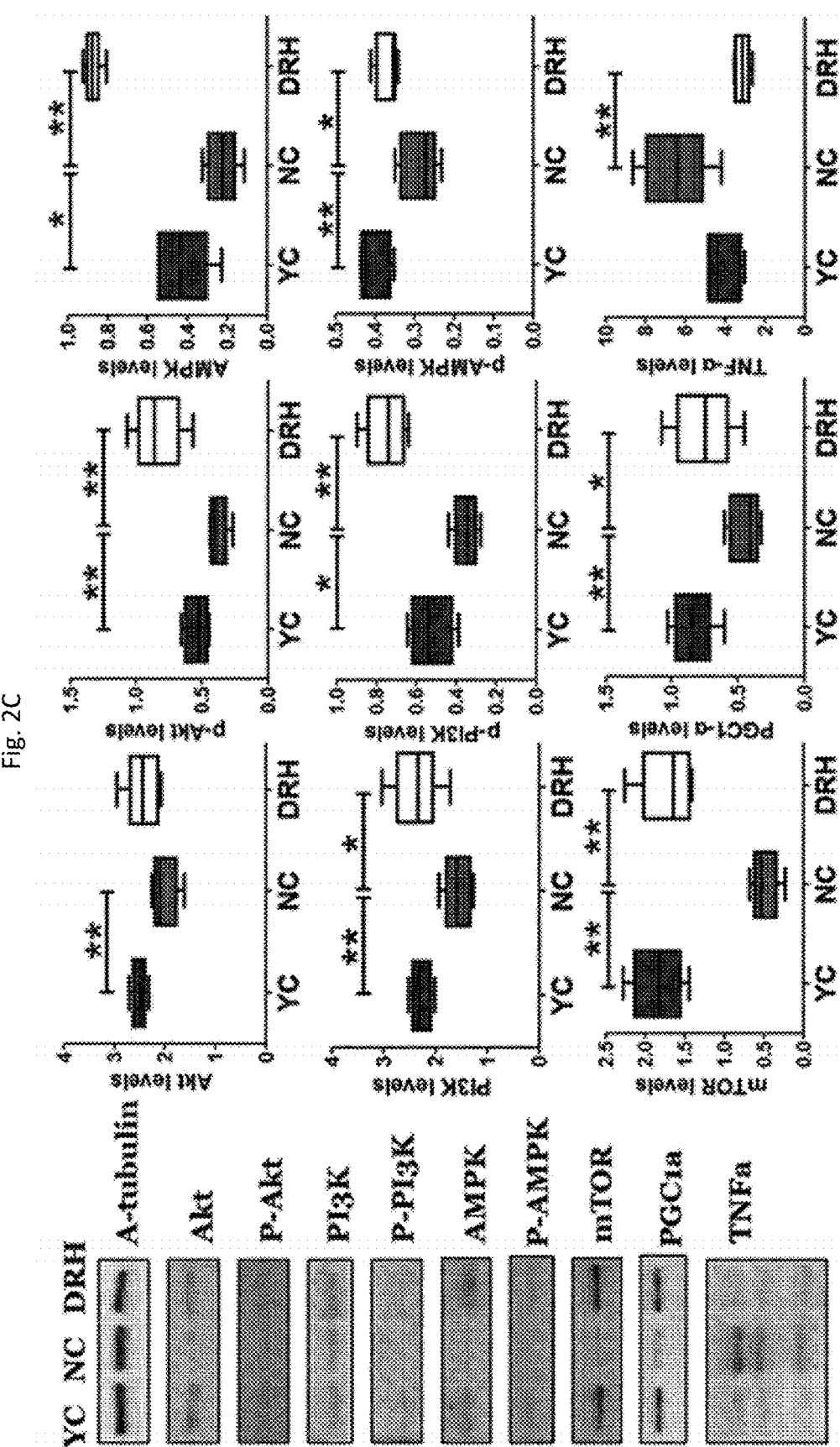

The cause of an increase in muscle strength was investigated by measuring the protein levels of Akt, AMPK, PI3K, mTOR, PGC1-α, and phosphorylated variants thereof. As a result, as shown in FIG. 2C, all of the protein expression factors significantly decreased in the NC group compared to the YC group. Supplementation with D-ribo-2-hexulose significantly increased gene expression in the DRH group compared to the NC group. TNF-α expression in the mice of the DRH group significantly decreased compared to that of the NC group.

Experimental Example 3: Effects of D-Ribo-2-Hexulose on the Transcriptional Response and Oxidative Phosphorylation of Gastrocnemius Tissue D-ribo-2-hexulose altered transcriptional responses and factors associated with oxidative phosphorylation in gastrocnemius tissue. Therefore, RNA sequencing (mRNA-seq) analysis was performed to investigate the transcriptome profile of the gastrocnemius tissue.

Differentially expressed genes (DEG) were identified using a fold change (FC) with a cutoff of 2 or more and a p-value of less than 0.05. As a result, as shown in FIG. 3A, supplementation with D-ribo-2-hexulose up-regulated two genes (i.e., cytokine inducible SH2-containing protein (CISH) and ceramide synthase 1 (CerS1)), and down-regulated six genes (i.e., Adiponectin, Adipsin, cell death-inducing DFFA-like effector c (CIDEC), Haptoglobin, Neuronatin, and stearoyl-coenzyme A desaturase 1 (SCD1)), compared to the NC group. To verify the mRNA-seq results, RT-PCR analysis and Western blotting were performed on DEG. As a result, as shown in FIG. 3B, it was confirmed that the results were consistent with those obtained by mRNA-seq analysis.

As shown in FIG. 3C, hepatic glucose-6-phosphatase (G6P) significantly decreased in the NC group compared to the YC group, but significantly increased in the DRH group compared to the NC group. Mitochondrial respiratory chain complexes, that is, Complexes I, II, III, and IV were analyzed through BN-PAGE. As a result, as shown in FIG. 3D, Complex IV significantly decreased in the NC group compared to the YC group, whereas supplementation with D-ribo-2-hexulose significantly increased Complex IV compared to the NC group.

Experimental Example 4: Effect of D-Ribo-2-Hexulose on Fat and Muscle Weight

As shown in FIG. 4A, supplementation with D-ribo-2-hexulose reduced fat weight, but no significant difference was found in the total weight of muscle tissue between the mice in the NC and DRH groups. However, it can be seen that the ratio of the total weight of muscle tissue to the total weight of adipose tissue significantly increased in the DRH group compared to the NC group.

As shown in FIG. 4B, the muscle triglyceride (TG) level increased with aging, but supplementation with D-ribo-2-hexulose significantly reduced this increase. Muscle total cholesterol (TC) and fatty acid levels increased in the NC group compared to the YC group. Nevertheless, there was no significant difference between the DRH and NC groups. Also, plasma TG and TC levels significantly increased in the NC group compared to the YC group, and this increase was improved by supplementation of D-ribo-2-hexulose. Plasma fatty acids were not significantly different between the YC and NC groups, but their levels significantly decreased in the DRH group compared to the NC group.

Experimental Example 5: Effects of
Supplementation with D-Ribo-2-Hexulose on
Inflammatory Cytokines, Antioxidant System,
Blood Glycogen, and Hormones As shown in FIG. 5A, the levels of inflammatory cytokines TNF-$\alpha$, interleukin-4 (IL-4), IL-1$\beta$, and IL-6 were not significantly different between the groups. When antioxidant enzyme activity was analyzed, as shown in FIG. 5B, liver GSH, PON, GR, and plasma PON activity significantly decreased in the NC group compared to the YC group, whereas supplementation with D-ribo-2-hexulose increased liver GSH-Px, PON, GR, and plasma PON activity. As shown in FIG. 5C, lipid peroxide and hydrogen peroxide contents, liver $H_2O_2$ content, a thiobarbituric acid reactive substance (TBARs), and an erythrocyte TBARs significantly increased in the NC group compared to the YC group. Supplementation with D-ribo-2-hexulose significantly reduced the liver $H_2O_2$ content.

As shown in FIG. 5D, the contents of muscle and liver glycogen were not significantly different between the groups. Fasting blood glucose levels in the NC group significantly increased from 8 to 12 weeks compared to the YC group, but significantly decreased at 12 weeks in the DRH group compared to the NC group.

As shown in FIG. 5E, testosterone levels significantly decreased in the NC group compared to the YC group, but did not show a significant difference between the DRH and NC groups. Cortisol levels significantly increased in the NC group but decreased in the DRH group, compared to the YC group.

The foregoing description of the present invention has been given for illustrative purposes only. Therefore, it will be understood that the description of the present invention may be easily modified into various forms without departing from the technical ideas and essential features of the present invention by those skilled in the art to which the present invention pertains. Therefore, it should be understood that the embodiments described above are illustrative and not limiting in all aspects.

INDUSTRIAL APPLICABILITY

D-ribo-2-hexose of the present invention is a sweetener capable of replacing sugar, is harmless to the human body, does not cause side effects in normal cells, thereby being safe for the human body, and may inhibit the degradation of myoprotein, and exhibit a muscle strength strengthening effect through an increase in muscle mass. Therefore, the present invention is industrially applicable because D-ribo-2-hexose of the present invention may be be effectively used in the prevention, alleviation, or treatment of sarcopenia.

The invention claimed is:

1. A method of alleviating or treating sarcopenia, comprising: administering a composition comprising D-ribo-2-hexulose as an active ingredient to a subject in need thereof.

2. The method of claim 1, wherein the D-ribo-2-hexulose satisfies one or more of the following characteristics:

a) increasing the expression of insulin-like growth factor 1 (IGF-1);

b) inhibiting myostatin expression;

c) inhibiting a reduction in muscle strength; or d) increasing muscle mass.

3. The method of claim 1, wherein the composition is a pharmaceutical composition or a food composition.

4. The method of claim 3, wherein the food composition is a health functional food composition.

* * * * *